(12) United States Patent
Barnes

(10) Patent No.: US 8,048,370 B1
(45) Date of Patent: *Nov. 1, 2011

(54) GERMICIDAL GENERATOR OF OZONE AND OZONITES

(76) Inventor: Ronald L. Barnes, Owens Crossroads, AL (US)

( * ) Notice: Subject to any disclaimer, the term of this patent is extended or adjusted under 35 U.S.C. 154(b) by 698 days.

This patent is subject to a terminal disclaimer.

(21) Appl. No.: 11/980,019

(22) Filed: Oct. 30, 2007

Related U.S. Application Data

(63) Continuation-in-part of application No. 10/867,860, filed on Jun. 15, 2004, now abandoned, which is a continuation-in-part of application No. 09/197,036, filed on Nov. 21, 1998, now Pat. No. 6,893,610, and a continuation-in-part of application No. 10/827,708, filed on Apr. 20, 2004, now Pat. No. 7,060,180, which is a continuation-in-part of application No. 10/061,752, filed on Feb. 1, 2002, now Pat. No. 6,723,233, which is a continuation-in-part of application No. 09/752,982, filed on Dec. 31, 2000, now Pat. No. 6,623,635, which is a continuation-in-part of application No. 09/418,915, filed on Oct. 15, 1999, now Pat. No. 6,342,154, said application No. 10/827,708 is a continuation-in-part of application No. 09/794,601, filed on Feb. 27, 2001, now abandoned, which is a continuation-in-part of application No. 09/752,982, filed on Dec. 31, 2000, now Pat. No. 6,623,635, said application No. 10/827,708 is a continuation-in-part of application No. 09/520,504, filed on Mar. 8, 2000, now Pat. No. 6,405,387, and a continuation-in-part of application No. 09/717,904, filed on Nov. 20, 2000, now Pat. No. 6,426,053, said application No. 10/867,860 is a continuation-in-part of application No. 10/176,299, (Continued)

(60) Provisional application No. 60/166,254, filed on Nov. 18, 1999, provisional application No. 60/066,119, filed on Nov. 21, 1997.

(51) Int. Cl.
*A61L 9/00* (2006.01)
*A62B 7/08* (2006.01)
*G01N 33/00* (2006.01)

(52) U.S. Cl. ............. 422/4; 422/120; 422/121; 436/135

(58) Field of Classification Search .................. 422/120, 422/121, 4; 436/135; 73/23.2
See application file for complete search history.

(56) References Cited

U.S. PATENT DOCUMENTS 4,990,311 A * 2/1991 Hirai et al. ........................ 422/4

(Continued)

*Primary Examiner* — Kevin Joyner
(74) *Attorney, Agent, or Firm* — Steven M. Clodfelter

(57) ABSTRACT

A combined ozone and ozonites generator and ozone eliminator is disclosed. The device uses different modes of operation to control generation or elimination of ozone, with some modes being used for generating ozonites, some of which are generally less reactive and provide more far reaching beneficial effects than ozone alone. The device uses 185 nm radiation to disassociate atomic oxygen leading to creation of ozone, and uses 254 nm radiation to disassociate ozone, reducing its concentration, with both processes leading to creation of ozonites. These effects are achieved by operating either lamp separately or by operating both lamps simultaneously while drawing air through a chamber containing the lamps.

7 Claims, 13 Drawing Sheets

Related U.S. Application Data filed on Jun. 20, 2002, now Pat. No. 6,967,008, which is a continuation-in-part of application No. 09/717,903, filed on Nov. 20, 2000, now Pat. No. 6,428,756, said application No. 10/176,299 is a continuation-in-part of application No. 09/794,601, filed on Feb. 27, 2001, now abandoned, which is a continuation-in-part of application No. 09/752,982, filed on Dec. 31, 2000, now Pat. No. 6,623,635, and a continuation-in-part of application No. 09/393,437, filed on Sep. 10, 1999, now Pat. No. 6,192,911, said application No. 10/176,299 is a continuation-in-part of application No. 10/061,752, filed on Feb. 1, 2002, now Pat. No. 6,723,233, which is a continuation-in-part of application No. 09/752,982, filed on Dec. 31, 2000, now Pat. No. 6,623,635, which is a continuation-in-part of application No. 09/418,915, filed on Oct. 15, 1999, now Pat. No. 6,342,154, said application No. 10/176,299 is a continuation-in-part of application No. 09/794,601, filed on Feb. 27, 2001, now abandoned, which is a continuation-in-part of application No. 09/752,982, filed on Dec. 31, 2000, now Pat. No. 6,623,635, and a continuation-in-part of application No. 09/393,437, filed on Sep. 10, 1999, now Pat. No. 6,192,911, said application No. 10/176,299 is a continuation-in-part of application No. 09/520,504, filed on Mar. 8, 2000, now Pat. No. 6,405,387, and a continuation-in-part of application No. 09/717,904, filed on Nov. 20, 2000, now Pat. No. 6,426,053.

(56) References Cited

U.S. PATENT DOCUMENTS 6,497,840 B1 * 12/2002 Palestro et al. ............... 422/24

* cited by examiner

GERMICIDAL GENERATOR OF OZONE AND OZONITES

CROSS-REFERENCE TO RELATED APPLICATIONS

This application is a continuation of Applicant's abandoned patent application Ser. No. 10/867,860, filed Jun. 15, 2004, which is a continuation-in-part of Applicant's patent application Ser. No. 09/197,036, filed Nov. 21, 1998, now U.S. Pat. No. 6,893,610, and which is incorporated herein in its entirety, and which claims the benefit of provisional patent application No. 60/066,119, filed Nov. 21, 1997.

The abandoned application Ser. No. 10/867,860 is also a continuation-in-part of Applicant's patent application Ser. No. 10/827,708, filed Apr. 20, 2004, now now U.S. Pat. No. 7,060,180 which is a continuation-in-part of Applicant's patent application Ser. No. 10/061,752, filed Feb. 1, 2002, now U.S. Pat. No. 6,723,233 which is a continuation-in-part of Applicant's patent application Ser. No. 09/752,982, filed Dec. 31, 2000, now U.S. Pat. No. 6,623,635, which is a continuation-in-part of Applicant's patent application Ser. No. 09/418,915, filed Oct. 15, 1999, now U.S. Pat. No. 6,342, 154. In addition, the application Ser. No. 10/827,708 filed Apr. 20, 2004 now U.S. Pat. No. 7,060,180 is a continuation-in-part of Applicant's abandoned application Ser. No. 09/794, 601, filed Feb. 27, 2001, which is a continuation-in-part of patent application Ser. No. 09/752,982, filed Dec. 31, 2000, now U.S. Pat. No. 6,623,635. In addition, Applicant's application Ser. No. 10/827,708 filed Apr. 20, 2004 now U.S. Pat. No. 7,060,180 is a continuation-in-part of patent application Ser. No. 09/520,504, filed Mar. 8, 2000, now U.S. Pat. No. 6,405,387, and a continuation-in-part of Applicant's patent application Ser. No. 09/717,904, filed Nov. 20, 2000, now U.S. Pat. No. 6,26,053.

In addition, the abandoned application Ser. No. 10/867,860 is a continuation-in-part application of Applicant's patent application Ser. No. 10/176,299 filed Jun. 20, 2002, now U.S. Pat. No. 6,967,008 which is a continuation-in-part application of application Ser. No. 09/717,903, filed Nov. 20, 2000, now patent number 6,428,756, which claims the benefit of provisional application No. 60/166,254, filed Nov. 18, 1999. The application Ser. Ser. No. 10/176,299 now U.S. Pat. No. 6,967,008 is also is a continuation-in-part of abandoned patent application Ser. No. 9/794,601, filed Feb. 27, 2001, which is a continuation-in-part of patent application Ser. No. 09/752,982, filed Dec. 31, 2000, now U.S. Pat. No. 6,623,635, which is a continuation-in-part of patent application Ser. No. 09/393,437, filed Sep. 10, 1999, now U.S. Pat. No. 6,192,911. The pending application Ser. No. 10/176,299 is also a continuation-in-part of patent application Ser. No. 10/061,752, filed Feb. 1, 2002, now U.S. Pat. No. 6,723,233, which is a continuation-in-part of patent application Ser. No. 09/752, 982, filed Dec. 31, 2000, now patent number 6,623,635, which is a continuation-in-part of patent application Ser. No. 09/418,915, filed Oct. 15, 1999, now U.S. Pat. No. 6,342,154, and which is a continuation-in-part of patent application Ser. No. 09/794,601, filed Feb. 27, 2001, now abandoned, which is a continuation-in-part of patent application Ser. No. 09/752, 982, filed Dec. 31, 2000, now U.S. Pat. No. 6,623,635, and a continuation-in-part of patent application Ser. No. 09/393, 437, filed Sep. 10, 1999, now U.S. Pat. No. 6,192,911, and a continuation-in-part of patent application Ser. No. 09/520, 504, filed Mar. 8, 2000, now U.S. Pat. No. 6,405,387, and a continuation-in-part of patent application Ser. No. 09/717, 904, filed Nov. 20, 2000, now patent number 6,426,053.

FIELD OF THE INVENTION

This application relates to a device for air purification and sterilization including use of different operational modes and different types of ultraviolet lamps for germicidal action and for controlling generation or elimination of ozone, and generation of different types and concentrations of ozonites, relative to concentrations of ozone. This allows optimization of purifying products and actions of various embodiments of Applicants invention to better deal with different contaminants and operating conditions.

BACKGROUND OF THE INVENTION

Air from a normal earth atmosphere consists primarily of diatomic nitrogen ($N_2$) followed by diatomic oxygen ($O_2$), water vapor, argon, carbon dioxide, and other trace gases generally not harmful to humans or other mammals at normal concentrations. However, both outdoor and indoor air may also contain many contaminants, with indoor air generally being more contaminated than outdoor air due to outgassing of building materials and furnishings such as rugs. These contaminants may include pathogens, pyrogens, other airborne particulates, other gases, or other substances. Airborne pathogens may include viruses, bacteria, and spores from molds and fungi. Within context of this application, pyrogens are defined as chemical compounds that can be oxidized, and include such chemical compounds as methane, ethane, butane, propane, toluene, alcohols, and numerous other compounds that can exist as a gas at normal room temperatures and pressures. Airborne particulates may include dust particles, metallic powders, pollen, and droplets of liquids. Other gases may include contaminant gases not found in a normal earth atmosphere but which are not normally subject to additional oxidation as are pyrogens. Other contaminant substances may include items not normally considered to be particulates or gases, such as animal hair and dander, other natural or synthetic fibers, dust mites and the like. Animal hair and dander, and some other fibers are able to harbor virus, bacteria, spores, or other potentially harmful substances, as well as being allergens to some people. It is generally desirable to have efficient and effective means of removing these contaminants in various spaces and volumes, including spaces concurrently or intermittently occupied by humans, pets, other animals, or plants.

Germicidal action of ultraviolet radiation of wavelengths generally shorter than about 400 nanometers (nm) is well known. Interaction of such ultraviolet radiation with many pathogens, generally by a mechanism of breaking chemical bonds within a molecular structure of a pathogen, may kill the pathogen or render it incapable of infection or reproduction. Generally, only brief direct exposures of susceptible bonding sites of a pathogen are needed in order to break chemical bonds and obtain germicidal benefits of ultraviolet radiation. This germicidal action has been incorporated, by use of so-called germicidal lamps capable of producing such ultraviolet radiation, into a number of products, including, for example, those used for sterilization of medical instruments, or other products used for sterilization of combs, clippers, and other tools used by barbers and beauticians. One key disadvantage of ultraviolet radiation for its germicidal action is that ultraviolet radiation may be blocked, or shadowed, by objects between a source of ultraviolet radiation and key interaction sites (e.g., molecular chemical bonds) within pathogens against which germicidal action is sought. Shadowing effects can result from airborne particulates as small as dust particles, and, in some cases, pathogens themselves or even large molecules can provide a shadowing effect for key interaction sites on the same pathogen or molecule, depending upon orientations of pathogens or molecules relative to a source of ultraviolet radiation.

Many germicidal lamps found in relatively inexpensive ultraviolet sterilization products make use of a mercury gas vapor discharge, also called mercury plasma, within an inexpensive silica glass tube, to provide an ultraviolet lamp. At least two predominant ultraviolet wavelengths are emitted from mercury plasma. These include an emission at approximately 254 nm, known as UV-C, and another shorter, thus more energetic, wavelength emission at approximately 185 nm, the latter being within a range of wavelengths from approximately 100 to 200 nm known as vacuum ultraviolet, or VUV, also referred to by some as "very ultraviolet." Although photons at 185 nm are more energetic than photons at 254 nm, total energy intensity of radiation emitted from mercury plasma at approximately 254 nm is typically about 25 times greater than total energy intensity radiated around 185 nm. When inexpensive silica glass is used for a lamp tube that contains a mercury plasma, ultraviolet radiation shorter than approximately 200 nm, including 185 nm emissions from mercury plasma, is strongly attenuated by the silica glass, but 254 nm radiation from mercury plasma is transmitted through the silica glass tube with very little attenuation.

In addition to its germicidal effects, ultraviolet radiation containing wavelengths near 254 nm also has an additional effect of accelerating breakdown, or disassociation, of ozone ($O_3$) molecules back into diatomic oxygen molecules ($O_2$) and atomic oxygen (O), an effect which is discussed more fully later herein with an explanation and disclosure of how this effect may be used in a novel application to achieve some objectives of the instant invention.

It is one object of the instant invention to take advantage of germicidal action of ultraviolet radiation to support germicidal purification of air within a treated area. It is a further objective of the instant invention to promote, for multiple reasons, in some embodiments and operational modes, turbulent airflow through a chamber or other region wherein air is exposed to ultraviolet radiation, with one purpose of turbulence being to cause tumbling of any pathogens in the air stream so as to increase likelihood that key interaction sites on or within pathogens will be exposed to ultraviolet radiation and not shadowed as described earlier herein.

It has been known for some time that ultraviolet radiation having a wavelength of approximately 100 nm to 200 nm can be used for generation of ozone. It does this by breaking bonds of diatomic oxygen molecules, leading to creation of freed oxygen atoms, some of which combine with diatomic oxygen molecules to form molecules of ozone. What has not been well recognized in literature, however, is that use of ultraviolet radiation to generate ozone can also lead to creation of another family of compounds that have come to be called ozonites, which are generally ozone reaction products. Ozonites are compounds that also have an oxidative capability similar to that of ozone, with some being more reactive than ozone, and some being less reactive than ozone. Ozonites thus have properties different from those of ozone alone, and different properties of various types of ozonites make it desirable to be able to separately control types and concentrations of ozonites, relative to concentrations of ozone alone, produced by use of ultraviolet radiation. Providing innovative means and methods by which relative production or removal of ozone and ozonites can be controlled are thus objects of the instant invention.

Another predominant ultraviolet emission line from a mercury plasma, namely that at approximately 185 nm, has been used in various applications for generation of ozone. However, in order to exploit 185 nm wavelength ultraviolet radiation from a mercury plasma for most practical applications, it is necessary to use a containment tube for the plasma that is made of a material transmissive to ultraviolet radiation at 185 nm wavelength. As noted earlier, silica glass attenuates 185 nm wavelength radiation very strongly. However, quartz remains relatively transmissive at this wavelength, with quartz of different purities and compositions having somewhat different transmissivities. Quartz tubes are also highly transmissive to 254 nm wavelength radiation resulting from mercury plasma. Thus, for generation of ozone and for various other purposes requiring shorter wavelength 185 nm ultraviolet photons, it has become a common practice to use mercury plasma ultraviolet lamps made with quartz tubes rather than silica glass tubes in order to permit transmission of more ozone-generating 185 nm wavelength radiation resulting from mercury plasma. However, other sources of ultraviolet radiation, including some lasers, having one or more wavelengths in a range of 100 to 200 nm could be used for generation of ozone and ozonites in various embodiments of the instant invention.

Quantity of ozone and, as discussed later herein, ozonites, produced from ultraviolet radiation as discussed above is somewhat a function of initial energy states or excitation of diatomic oxygen molecules and other constituents of air flowing through chambers wherein air is exposed to ultraviolet radiation having wavelengths sufficiently short to cause breakdown of diatomic oxygen molecules. These initial energy states are affected by air temperature, pre-excitation of oxygen molecules and other constituents in air by electric and magnetic fields present in an exposure chamber, and recent history of exposure of constituents of air to ultraviolet and visible radiation at multiple wavelengths. It is thus another object of the instant invention to exploit one or more of these means to enhance initial energy states of a portion of diatomic oxygen molecules and other constituents of air so as to enhance efficiency and yield of processes disclosed herein for using ultraviolet lamps and other features of the instant invention to create ozone and ozonites, and to control types of ozonites produced and concentrations of ozonites relative to concentrations of ozone produced for a given application.

Although, as noted above, it has become common practice to use quartz tube mercury plasma lamps for generation of ozone, and less expensive silica glass tube mercury plasma lamps for many germicidal applications, what has not been fully recognized and previously exploited in the art are relative roles of different ultraviolet wavelength regimes in generation of this separate class of compounds called ozonites. As inferred earlier, ozonites have useful properties and applications which can be complementary or separate from applications of ozone alone. These useful properties and applications of ozonites, beyond those of ozone alone, are explained further below.

Ozone molecules themselves are highly reactive leading to many uses in purification and sanitization of air, liquids, and surfaces, generally via oxidative reactions with contaminants, including pathogens and pyrogens. Reactions of ozone with many pathogens leads to an effect called lysing, wherein ozone causes an oxidation reaction with bonds of molecules in cell walls of many pathogens, leading to a rupture of their cell walls, resulting in breakup and demise of the pathogen.

Reaction of ozone with many pyrogens is generally an oxidative reaction similar in its products to those of normal combustion (e.g., carbon dioxide, water vapor, and other oxides). Ozone is thus useful in breaking many pyrogen contaminants down into less reactive and harmless compounds. However, in high concentrations, ozone may cause respiratory irritation and other undesirable effects, in humans and pets. Also, ozone molecules are themselves unstable, having a half-life of only a few hours.

The highly reactive and short-lived nature of ozone molecules are both an advantage and a limitation of ozone depending upon how it is used for air purification. An advantage is that ozone may be used for a short-term, high concentration treatment (called a shock treatment) of an area, such as one or more rooms in a house, to obtain oxidative benefits of ozone when humans or pets are not present, with ozone concentration levels decaying rapidly to levels safe for humans and pets soon after generation of ozone is terminated. One objective of the instant invention is to provide a capability for generation of sufficient levels of ozone to permit use of ozone in providing such short term treatments of limited areas. It is another objective of the instant invention to provide a capability for quickly destroying residual ozone in an area so as to more rapidly reduce ozone concentrations to levels safe and comfortable for human habitation.

A limitation of use of ozone is that, due to ozone's high reactivity, it will tend to react quickly with substances nearest a source of ozone generation, so that concentrations fall off quickly with distance from an ozone generator. Its high reactivity and its instability also mean that ozone itself provides little long-term or residual beneficial oxidative effect in a treated area. However, it has been cited in ozone-related literature that some byproducts, called ozonites, of interaction of ozone with other molecules or substances in liquid or gaseous media are also capable of oxidative or other beneficial reactions. Ozonites resulting from interactions of ozone and atomic oxygen with constituents of a normal airflow through an ozone-producing generator, as might be typical of normal household air, are generally less reactive and more stable than ozone molecules, but some ozonites may be more reactive than ozone alone. For example, some ozonites include hydroxyl radicals as well as other ionized or non-ionized molecules that are more reactive than ozone itself. (Use of ozonites to create additional oxidative reactions has been called "advanced oxidation" or "advanced oxidation processes" by some authors in ozone-related literature.) Ozonites that are less reactive than ozone molecules tend to persist longer and propagate further from an ozone generating source than ozone molecules, and are thus capable of producing beneficial effects of oxidation of contaminants and pathogens for longer periods after generation, and at greater distances from a generator, than ozone alone. These less reactive ozonites are also generally less likely than ozone to cause irritation in exposed humans and animals (e.g., pets). In contrast, ozonites such as hydroxyl radicals that are more reactive than ozone will tend to react even more rapidly than ozone with pyrogens, pathogens, and other contaminants and thus tend to be even shorter-lived with less far-reaching effects than ozone alone. However, this more highly reactive class of ozonites has another very important benefit—namely, an ability to oxidize some compounds, particularly those known as refractory organics, defined below, that are generally less susceptible to oxidation by ozone alone, particularly at normal room temperatures and pressures.

Pyrogens may include refractory organics such as nitrobenzene, phenols, 2,4,6-trinitrotoluene (TNT), atrozine, chlorobenzenes, and other compounds that are generally less susceptible to direct oxidation by ozone and atomic oxygen at normal room temperature and pressure. It has been found that many of these refractory organics are susceptible to oxidation, at normal room temperature and pressure, by some ozonites, particularly those ozonites containing hydroxyl radicals, ozonites containing halogens, and other highly reactive forms. These highly reactive ozonites may be created by interaction of ozone ($O_3$) or free atomic oxygen (O) with substances such as water vapor, hydrogen peroxide, or halogen molecules or compounds present in an air stream in which ozone is being created by VUV radiation, or in which ozone is being destroyed by UV-C radiation. Free atomic oxygen (O) may be created from breakdown of diatomic oxygen ($O_2$) molecules by VUV radiation during creation of ozone, or during breakdown of ozone molecules by UV-C radiation.

Thus, in addition to obtaining sterilization benefits of ultraviolet radiation, and purification and sanitization benefits of ozone alone, it is an additional object of the invention to provide novel and unobvious features to promote generation of ozonites and, in some cases and applications, to enhance relative concentrations, in treated areas, of ozonites as compared to ozone alone.

Additionally, in different embodiments of the instant invention, or in different operational modes of a given embodiment, it is a further object of the instant invention to provide features for enhanced generation, in some cases, of ozonites less reactive than ozone alone, and in other cases, to provide additional novel and unobvious features to enhance generation of ozonites more reactive that ozone alone.

As will be shown later herein, generating enhanced concentrations of ozonites, as compared to ozone alone, is accomplished in the instant invention by novel, but simple, combinations, in one or more devices in different embodiments, of filters or humidifiers or injectors to pre-treat an incoming air stream, different types of ultraviolet lamps in one or more exposure chambers, carbon canisters or other post-exposure filters to post-process or treat an exiting air stream, one or more fans to move an air stream through a purification unit and help control whether airflow is laminar or turbulent within the unit, and control systems which may provide for multiple modes of operation. Pre-treatment of an air stream may involve use of filtration to remove larger fibers or larger particulates from the air stream. Pre-treatment may also involve evaporation or injection of water vapor, hydrogen peroxide, catalysts, or other substances into an incoming air stream in order to modify or control some reactions that take place within a purification unit of the instant invention or within an exiting air stream or within an area or volume being treated by a purification unit of the instant invention. Water vapor or other agents may be added via use of Seltzer pads that provide a medium for wicking and evaporation of selected substances into an air stream. Water vapor or other agents could also be added to an air stream via use of high-pressure atomizing nozzles, via use of ultrasonic action, as is common in some household humidifiers, via use of heating to produce steam or other vapors, or by other means.

In addition to contributing to creation of more reactive ozonites containing hydroxyl radicals, enhanced levels of water vapor in an output air stream, and consequently in an area being treated, will tend to cause spores of molds or fungal materials to open up, or bloom, causing them to be much more susceptible to reaction and destruction by ozone or ozonites in air. A similar effect is also generally true for biofilms.

Various combinations of ultraviolet lamps, including one or more lamps that provide ultraviolet wavelengths that tend to help produce ozone and/or including one or more lamps that produce wavelengths that tend to break down ozone, may be used simultaneously within a chamber, or sequentially along a flow path, or in an alternating fashion, perhaps controlled by a timer, in order to help control generation and destruction of ozone, and production of ozonites, within a purification unit of the instant invention. Carbon canisters or other devices may be used to treat an air stream in a post-exposure filtration or other post-exposure treatment after it has flowed through one or more chambers and been exposed to one or more ultraviolet lamps in order to control generation, destruction, or release of ozone, ozonites, or other substances within an air stream. Post-exposure treatment may be for a purpose of further controlling concentrations of ozone, ozonites, or other substances exiting a purification unit of the instant invention. Heat may be added, via an electrical resistant heater or another source of heat, in order to help control reaction rates that help lead to desired changes in an exiting air stream. Other parameters or conditions that determine efficiency of a purification unit of the instant invention in producing ozone or ozonites, or both ozone and ozonites, include dimensions of one or more exposure chambers containing ultraviolet lamps, particularly VUV lamps used in various embodiments, and whether airflow through such chambers is turbulent or laminar in the vicinity of ultraviolet lamps, particularly any VUV lamps used in various embodiments. Dimensions of exposure chambers are important to controlling relative proportions of ozone and ozonites produced since shorter wavelength VUV radiation used to produce ozone is attenuated in air much more than longer UV-C wavelength radiation, which tends to break down ozone. Thus, a chamber with smaller dimensions surrounding a VUV tube, nominally one to two centimeters, will tend to produce a higher output of ozone, and a higher concentration of ozone relative to ozonites. A chamber with larger dimensions will tend to permit relatively more exposure of ozone to UV-C radiation from either a VUV tube or from a germicidal tube which primarily produces UV-C radiation, leading to a greater reduction in output of ozone relative to various ozonites. In addition, a laminar flow of air over a VUV tube will tend to cause creation of a higher concentration of ozone since there is less opportunity for ozone created in a zone close to a VUV tube to mix with other constituents of air and undergo reactions leading to reductions in ozone concentrations and increases in ozonites concentrations. Turbulent flow, however, causes better mixing, with other constituents of an air stream going through an exposure chamber, of ozone created near a surface of a VUV tube, thereby reducing concentration of ozone and enhancing production of ozonites that contribute to advanced oxidation. Bladed fans will tend to produce more turbulent flow than squirrel cage blowers. Use of reflectors around a UV-C tube (i.e., germicidal tube) can increase exposure of ozone to reflected UV-C radiation, thus reducing concentration of ozone but increasing concentration of ozonites produced. Various controls, or an overall control system, may be used to control use or sequencing of individual components of any given embodiment of the instant invention. Any given embodiment may contain some or all components and appropriate controls for different modes of operation as described above and in more detail later herein in order to help optimize a given embodiment for a particular application or set of applications.

Different modes of operation take advantage of different effects of different wavelengths of ultraviolet radiation to independently promote generation or destruction of ozone relative to ozonites, and to add substances or remove substances from an intake air stream or an exiting air stream to further control types and concentrations of ozonites, ozone, and other products of reactions that take place within a purification unit of the instant invention. Destruction of ozone and control of relative concentrations of ozone and ozonites takes advantage of a property of UV-C radiation mentioned earlier, namely, an ability of UV radiation having a wavelength of approximately 254 nm to break bonds within an ozone molecule, resulting typically in creation of a diatomic oxygen molecule and freeing of an oxygen atom, which then reacts rapidly with other molecules or substances in air. Thus, various embodiments of the instant invention may be optimized for applications primarily related to removal of ozone rather than generation of ozone. For example, in some environments where ozone generators of various types may be used to provide relatively high concentrations of ozone in specific areas or substances, especially in a confined space occupied by humans or other animals or plants, release of ozone into ambient air from materials or substances being treated may cause ozone concentrations to exceed safe or desirable levels. This may occur, for example, in situations such as use of ozone to control growth of fungal organisms on grain stored within a warehouse or grain elevator, or use of ozone in a jetted hot tub or spa, as described in Applicant's U.S. Pat. No. 6,723,233, to control contaminants within water or within plumbing or other fixtures associated with a hot tub or spa. In such cases, embodiments of the instant invention may be used in a free-standing mode within ambient air from which ozone removal is desired, or embodiments may be tailored, for example, to interface with locations, such as vents, where ozone is released from materials or substances being treated so as to further increase effectiveness of ozone destruction or control. Such embodiments may make use of one or more standalone or integrated ozone sensors, such as revealed herein, to control operation of embodiments intended for ozone removal, or such embodiments may simply be controlled manually or by use of timers.

For some applications, to further control concentrations of specific ozonites or other compounds produced within or exiting from a purification unit of the instant invention, alternate vapor discharge or plasma lamps, or lasers, or other sources of radiation capable of producing different radiation wavelengths to disrupt molecular bonds in those specific ozonites or other compounds to be controlled may be selected and integrated into alternate embodiments of the instant invention. Such lamps may be based on substances other than mercury, or contain compounds in addition to mercury, that are capable of producing radiation of desired wavelengths. For containment tubes, such lamps may also use materials, other than silica glass or quartz, that have less attenuation at desired wavelengths.

Certain embodiments of the instant invention may also make use of hybrid ultraviolet tubes, such as disclosed in Applicant's U.S. Pat. No. 6,426,053, in order to obtain at least two additional benefits. Such hybrid tubes use a coil of wire wrapped in a helical fashion down the length of a plasma containment tube, generally made of quartz, to generate electric and magnetic fields. These fields create a theta pinch effect on plasma within the tube that enhances efficiency in generation of radiation from plasma in the tube by increasing collisions, within the pinched plasma, among ionized components of the plasma and by reducing collisions of charged particles contained in the tube with walls of the tube. Such collisions with tube walls cause non-productive loss of energy from plasma in the tube and also contribute to undesirable heating of walls of a containment tube. A secondary benefit of a hybrid tube is that electric and magnetic fields, which are most intense immediately adjacent to the wires surrounding a hybrid tube, also contribute to pre-excitation of diatomic oxygen molecules and other constituents of air being treated so as to enhance efficiency of generation of ozone and ozonites by VUV radiation being emitted from such a tube, which radiation is also most intense in areas immediately adjacent to the tube. Other benefits, applications, and alternative embodiments for hybrid tubes are described in the referenced patent.

DETAILED DESCRIPTION OF THE DRAWINGS

Figure 1:
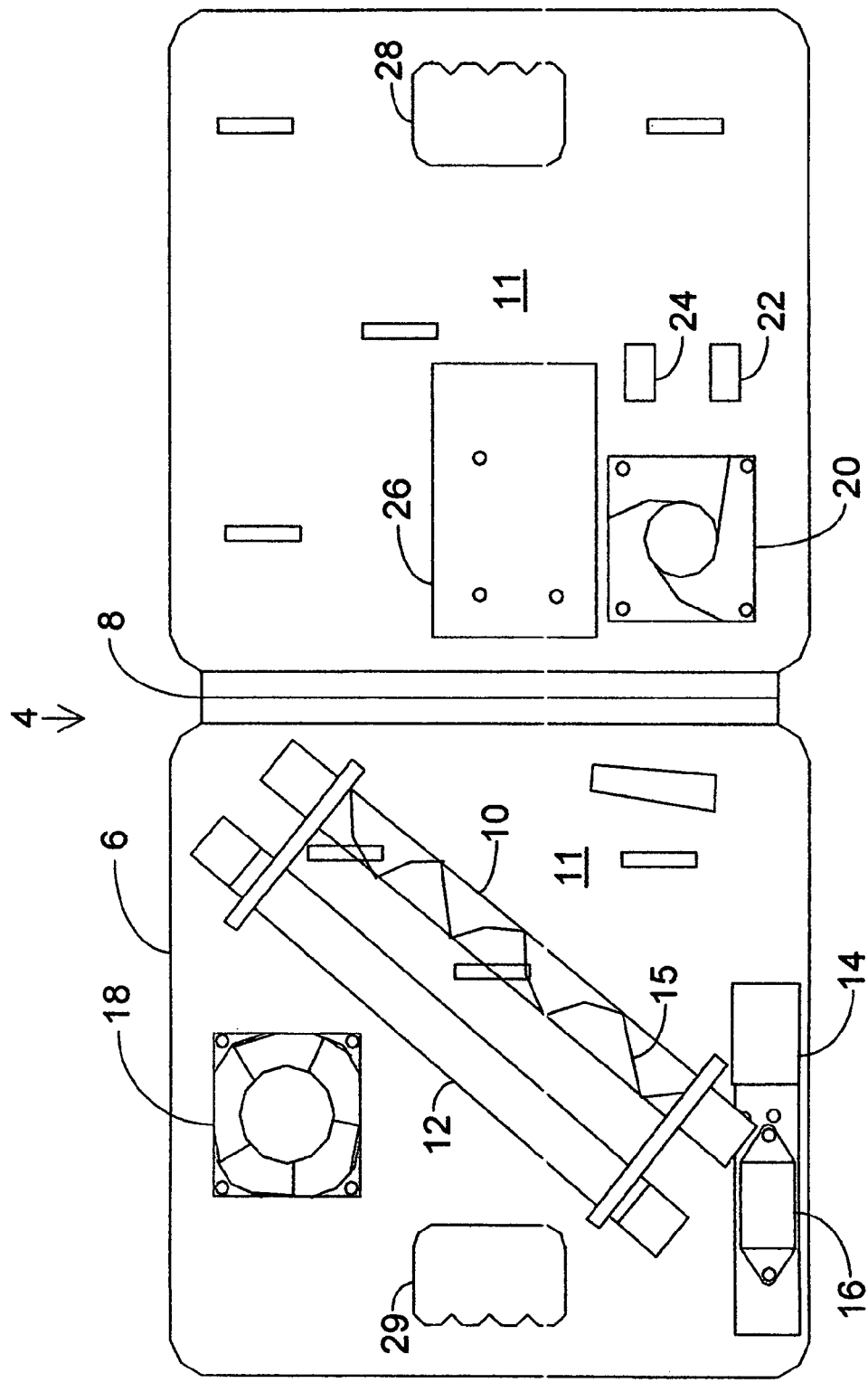
FIG. 1 is a diagrammatic view of one embodiment of the instant invention, components thereof being shown in a typical layout within an opened housing enclosure.
Figure 2:
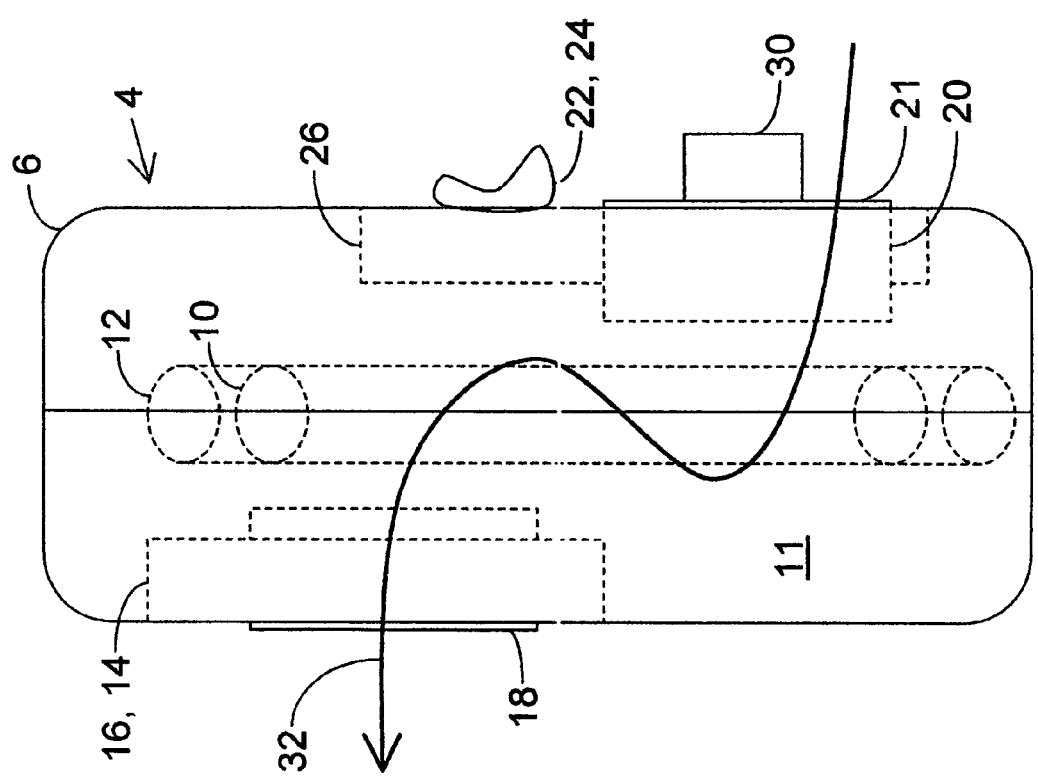
FIG. 2 is a diagrammatic side view of one embodiment of the instant invention showing a chamber and air passageway formed when the housing of FIG. 1 is closed.

Referring to FIG. 1, a typical primary embodiment 4 of the instant invention comprises two ultraviolet lamps 10, 12 and associated ballasts 14, 16 positioned within a housing 6 that, when closed, provides an enclosed chamber 11 for containing lamps 10, 12. Such an embodiment will typically include one or more fans 18, 20, for promoting air flow through chamber 11, and also include switches 22, 24, one or more timers 30 or other controls to control different modes of operation of the instant invention, and one or more additional enclosures or junction boxes 26 to contain electrical components or provide protective enclosures for wiring junctions. Housing 6 in general may be opaque to ultraviolet radiation and provide suitable seals and baffles to prevent escape of potentially eye-damaging radiation when closed and in operation. Alternately, in enclosed volumes such as fan enclosures for furnaces and air conditioners, water cooling towers and other similar locations where humans and pets are not exposed to ultraviolet radiation from such a source, housing 6 may be transparent to ultraviolet radiation where germicidal effects are to be obtained. Housing 6 should also be resistant to exposure to ultraviolet radiation without significant degradation. In some embodiments, housing 6 may be made in essentially one piece of an injection molded or blow-molded plastic of an ultraviolet-resistant character with a pliable plastic hinge 8, or it may be of other materials, or in separate halves joined by hinges, or in multiple other forms and different materials. A washable or replaceable filter 19 (FIG. 3) may be used on an airflow intake 21 (FIG. 2) to remove larger impurities. One lamp 12 may be a standard mercury vapor gas discharge lamp, also called a mercury plasma lamp or germicidal lamp, capable of emitting ultraviolet radiation that contains a predominant wavelength component around 254 nm, or UV-C as defined earlier, such as is commonly found in various sterilizing devices. Such lamps typically use a containment tube or envelope made of standard silicate glass that blocks transmission of shorter wavelength components (e.g., 185 nm) of radiation, or VUV, as defined earlier, from a mercury plasma discharge. A second lamp 10 may also be a mercury vapor plasma lamp, but this lamp 10 uses a quartz containment envelope instead of silicate glass so as to permit transmission of 185 nm ultraviolet radiation produced by a mercury vapor discharge, in addition to permitting transmission of 254 nm ultraviolet radiation also produced by such a discharge. This VUV ultraviolet lamp 10 may also make use of an electrical winding 15 around lamp 10, as described in Applicant's U.S. Pat. No. 6,426,053, configured so as to produce a theta pinch effect on mercury vapor plasma within the tube, thereby reducing collisions of electrons with sidewalls of the containment tube, which reduces heating of the containment tube and its surroundings and enhances efficiency in production of desired UV radiation. In the embodiment of FIG. 4, all components are integrated into a plastic case or housing 6 hinged on one side 8 so that housing 6 may be opened for installation or servicing of components. In the embodiment illustrated in FIG. 4, molded cutouts 28, 29 in housing 6 provide a carrying handle 29 when closed, and slide or flip-type latches (not illustrated) or other devices or methods as should be apparent to those skilled in the art may be used to keep housing 6 closed. As noted above, when closed, as illustrated in FIG. 2, housing 6 creates a chamber 11 that encloses and protects lamps 10, 12 and other components from damage while also protecting outside environments from direct exposure to ultraviolet radiation produced by lamps 10, 12, and from high voltages sources 14, 16 that may be used to power lamps 10, 12. In different operational modes, either or both lamps 10, 12 may be ON, creating different effects and different concentrations of output products. Housing 6 also includes one or more fans 18, 20 and provides a chamber 11 that also serves as a passageway for general movement of air through unit 4, as illustrated by a curved arrow 32 in FIG. 2. Airflow 32 may be generally laminar or turbulent, depending upon desired effects or products, as selected by alternative modes of operation. Operating unit 4 with both fans 18, 20 on at relatively high speed will generally create turbulent (versus laminar) flow in vicinity of lamps 10, 12, so as to improve generation and mixing of ozone and enhance reactions of ozone with other constituents in air flow 32. Enhanced mixing provided by turbulent flow promotes reactions of ozone and atomic oxygen produced by VUV radiation with contaminants so as to enhance purification action of unit 4, and also promotes generation of ozonites.

Figure 3:
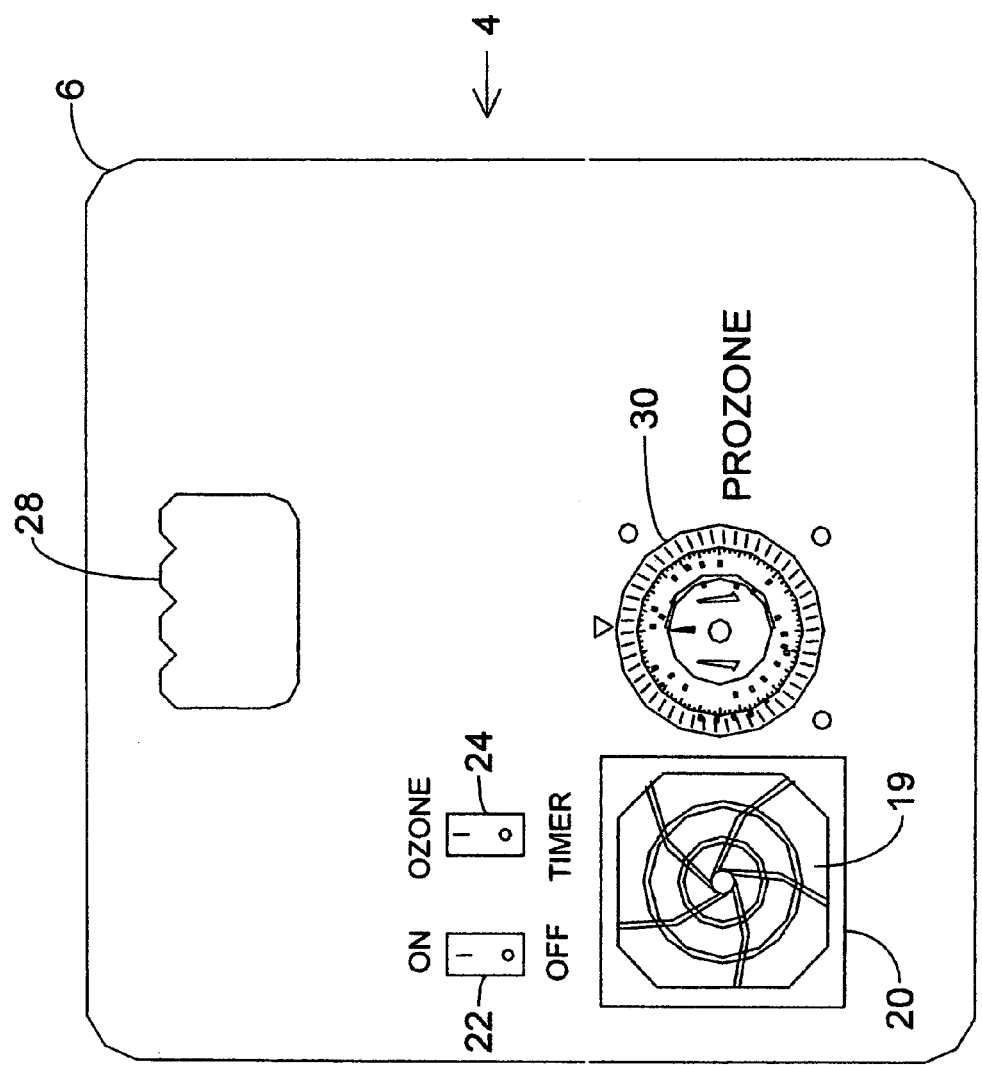
FIG. 3 is a diagrammatic view of a front of one embodiment of the instant invention showing an intake fan and switches and timer controls.
Figure 4:
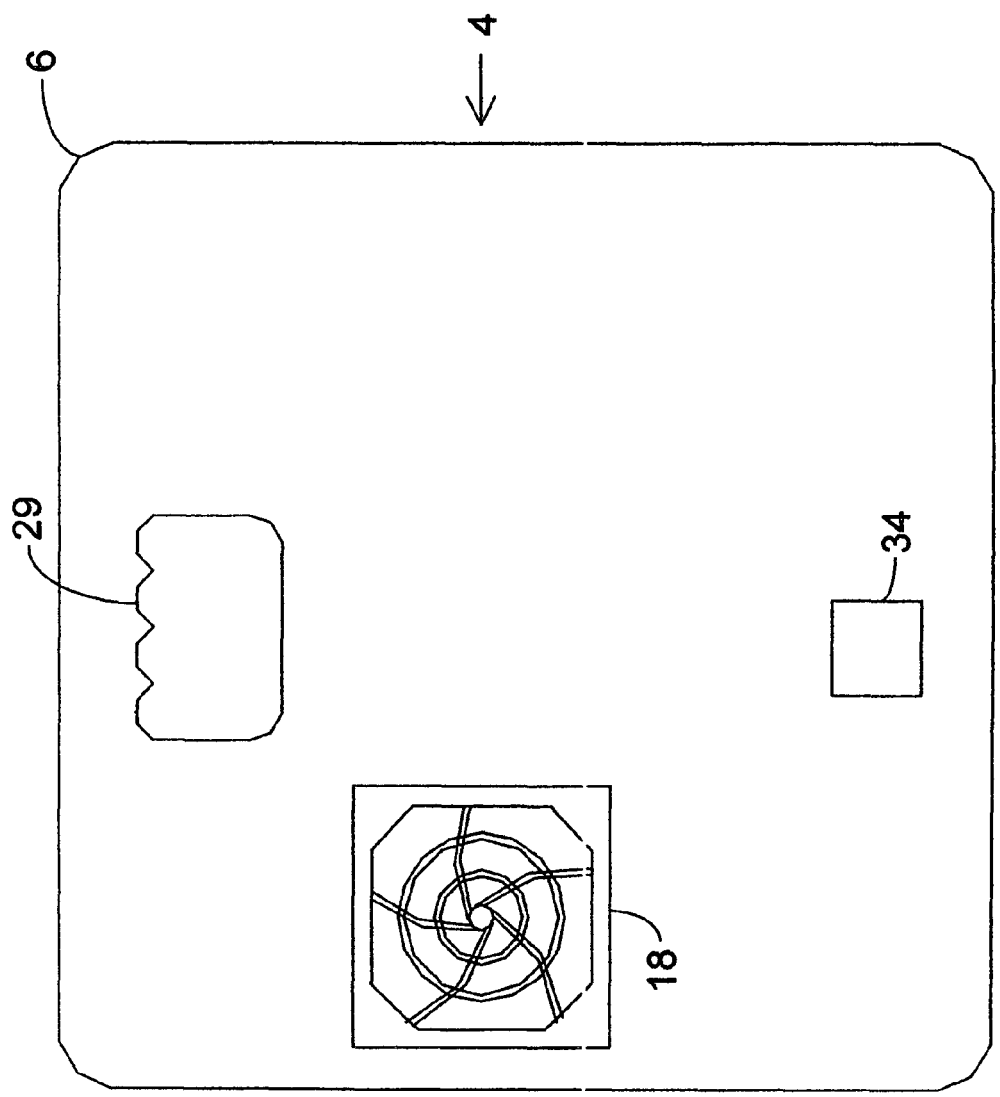
FIG. 4 is a diagrammatic view of a rear side of one embodiment of the instant invention showing an exhaust fan and power connection port.

FIG. 3 provides a view of a front of a primary embodiment of the instant invention showing how a master on-off switch 22 and an "OZONE" versus "TIMER" mode selection switch could be located on unit 4. This view also illustrates how a fan 20 and a timer 30, and an opening providing a handle 28 could be positioned for easy access and control by a user of unit 4.

FIG. 4 provides a view of the back of a primary embodiment of the instant invention showing a second fan 18 and a plug 34 where a power cord may be attached, in addition to a view of the back side of a molded-in handle 29. Power may be provided through a detachable power cord, as provided for by a plug 34, or power cord could be run directly through housing 6 using a suitable grommet or other protection, depending upon safety or regulatory requirements of governmental regions where an embodiment of the instant invention may be used.

Controls used in various embodiments of the instant invention may include simple manual switches 22, 24 and one or more timers 30, or controls may consist of more integrated and sophisticated electronic controls, including micro-processor controls. In most embodiments, primary functions of controls include enabling an air purification device of the instant invention to be operated in any of several modes, generally with at least one mode providing continuous generation of ozone, another mode providing a timer for timed intervals of ozone generation, and another mode providing germicidal action and ozone extinction rather than ozone generation. In modes providing for continuous or timed generation of ozone by use of one or more VUV lamps, controls may also provide for simultaneous or sequenced operation of one or more UV-C lamps in order to control quantities or concentrations of ozone produced and released, or to control ratios of ozone to one or more ozonites produced. In some embodiments, ON and OFF cycling, or power levels, of one or more fans, or separate cycling of one or more VUV lamps, or one or more UV-C lamps, may be controlled by use of one or more ozone sensors, as illustrated later herein.

Figure 5:
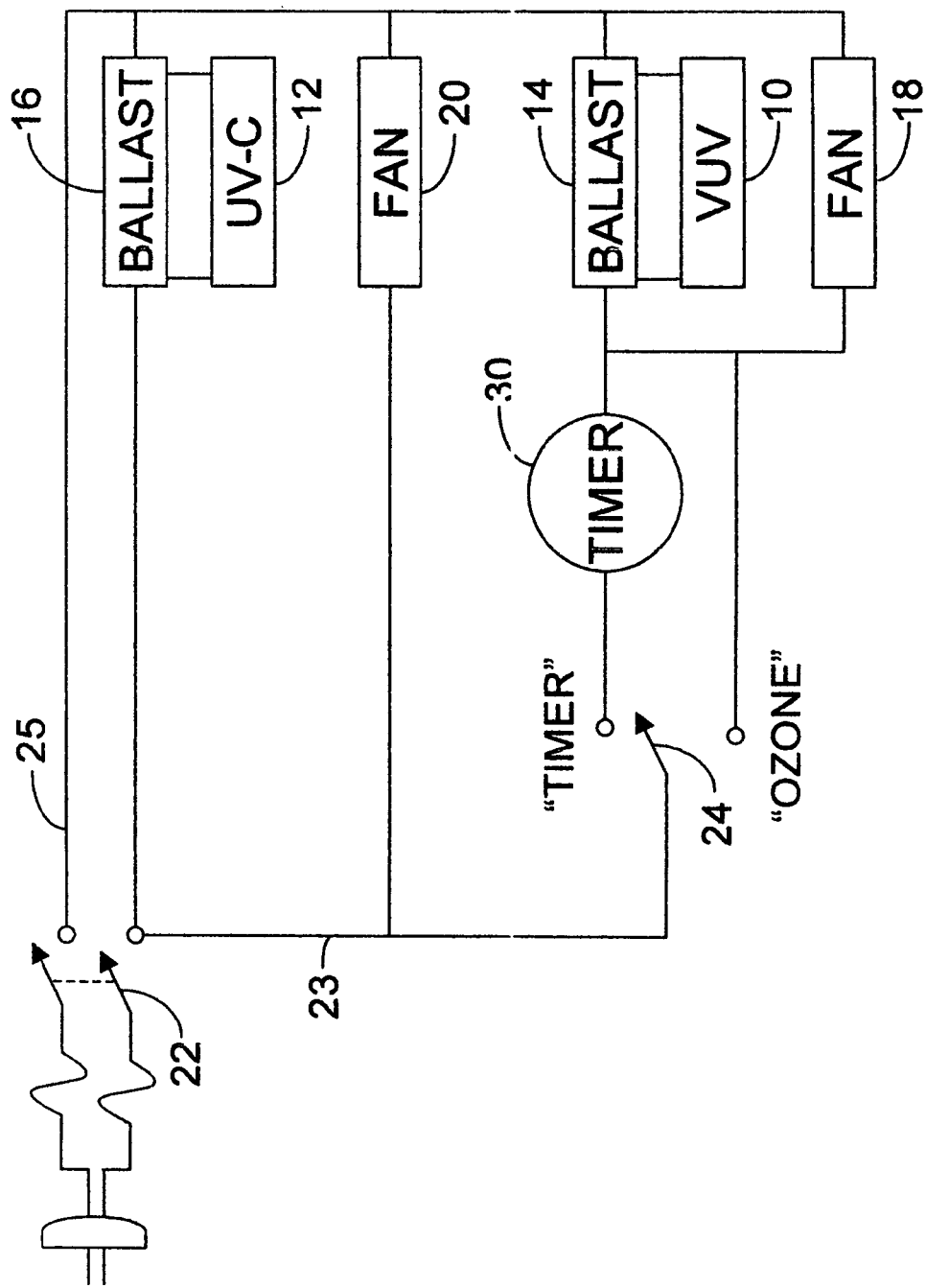
FIG. 5 is a block diagram illustrating particulars of construction of the instant invention.
Figure 7:
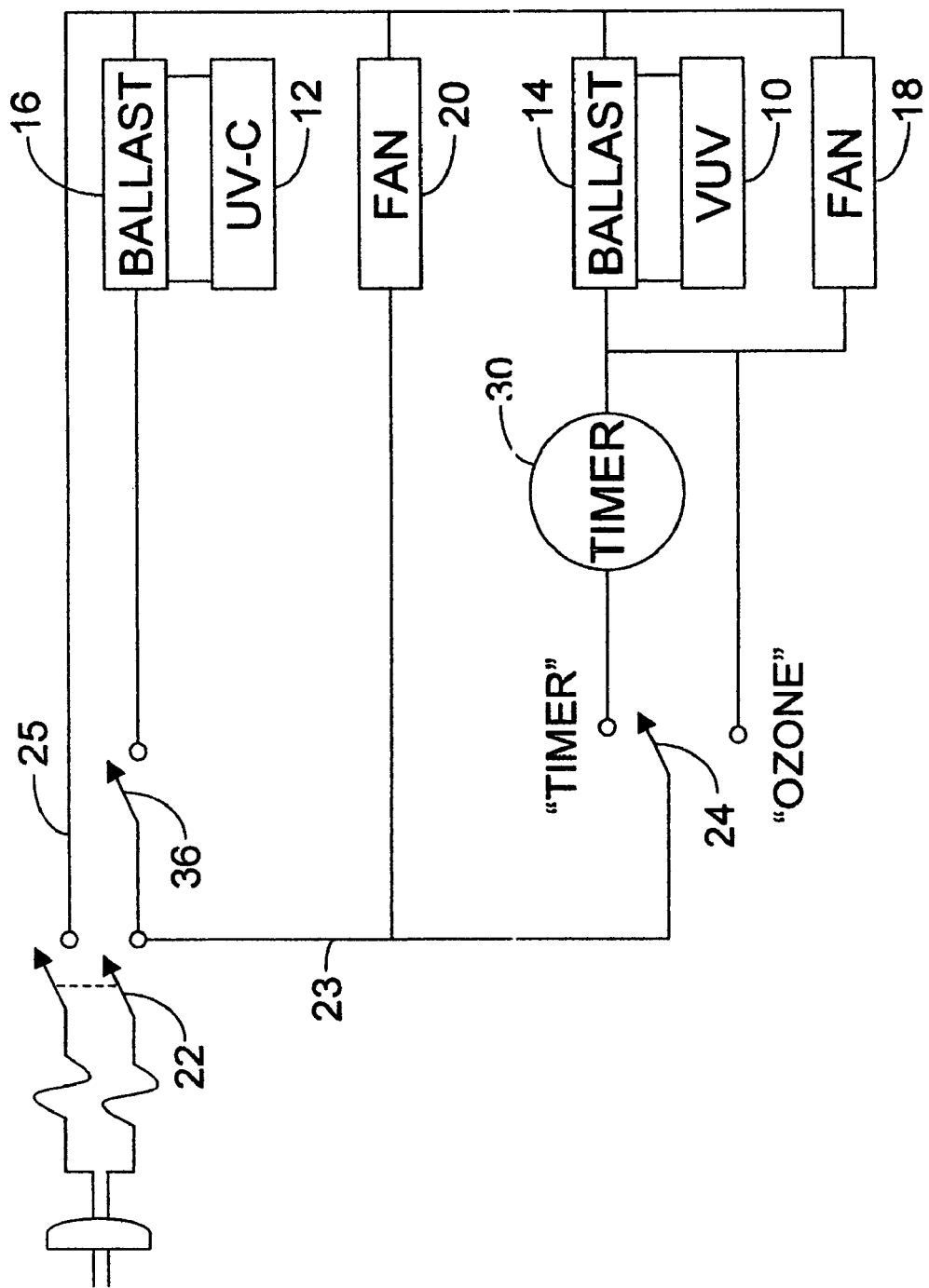
FIG. 7 is a block diagram of one embodiment of the instant invention.

As noted above, and referring back to a primary embodiment as described in FIG. 1, FIG. 2, FIG. 3, and FIG. 4, one key difference between some operating modes is whether either one or both types (i.e., VUV or UV-C only) of ultraviolet lamps 10, 12 are switched ON. In such a primary embodiment, controls may be implemented, as illustrated in FIG. 5, to support at least three modes of operation, referred to herein as CONTINUOUS OZONE OUTPUT, TIMED OZONE OUTPUT, and GERMICIDAL ONLY with a germicidal lamp 12 energized in all three modes. This embodiment, with a UV-C lamp energized any time unit 4 is switched ON with master on-off switch 22, may be preferred, for example, for a typical household application wherein a consumer wishes to place a unit 4 in a "CONTINUOUS OZONE OUTPUT" mode leading to generation of uncomfortable concentrations of ozone that may otherwise occur were it not for ozone removal capabilities of UV-C lamp 12. As also described earlier, embodiments that do not have special features to enhance generation of more active ozonites will tend to produce higher levels of less active types of ozonites when operated in modes wherein a UV-C lamp 12 is energized along with a VUV lamp 10. Such embodiments and operational modes may generally be preferred for typical household environments wherein there is less need to deal with pyrogens such as refractory organics, and wherein farther reaching and longer lived benefits of less reactive types of ozonites are preferred. However, for some household applications, or for other applications, embodiments with an additional control switch 36, as illustrated in FIG. 7, could provide at least a fourth mode, e.g., a "MAXIMUM OZONE OUTPUT" mode, with only a VUV lamp 10 energized, and any UV-C lamps 12 switched off. Such an embodiment and mode would reduce ozone extinction and lead to more rapid production of higher concentrations of ozone, and lower concentrations of ozonites, than is produced by control modes of a primary embodiment as illustrated in FIG. 5. Alternatively, a mode employing only a VUV lamp 10 could be implemented as an operational mode in a simpler embodiment.

Operation and effects of controls, as illustrated in FIG. 5, of a primary embodiment of the instant invention are described in more detail as follows. In a "CONTINUOUS OZONE OUTPUT" mode, both lamps (VUV and UV-C) 10, 12 are on. As air is drawn by fans 18, 20 through a filter 19 and then through a chamber 11 so as to circulate generally around enclosed lamps 10, 12, several different reactions and interactions occur, all generally contributing to air purifying capabilities of an air purification unit 4 of the instant invention.

In one interaction, as noted earlier herein, 185 nm ultraviolet radiation from a quartz VUV lamp 10 breaks molecular bonds in some diatomic oxygen ($O_2$) molecules flowing through chamber 11, developing monatomic oxygen atoms (O) that combine generally with other diatomic oxygen ($O_2$) molecules (but possibly also with other monatomic oxygen atoms) so as to create molecules of ozone ($O_3$). Both monatomic oxygen atoms and ozone thus created will immediately begin to interact via oxidation reactions with pathogens, pyrogens, and other substances in air flowing through chamber 11, and will continue to react with pathogens, pyrogens, and other substances after exiting an air purification unit 4, including pathogens, pyrogens, and other substances suspended in air that went through chamber 11 as well as pathogens, pyrogens, and other substances, in air surrounding an exit of a unit 4 and elsewhere in an area being treated, that did not flow through air purification unit 4. These purifying interactions with pathogens, pyrogens, and other contaminants in air will continue until all ozone molecules and freed oxygen atoms have been consumed in such reactions, or until ozone concentrations have been diminished through instability and spontaneous decay.

In another interaction, as incoming air circulates through chamber 11 and around lamps 10, 12, ultraviolet radiation from both lamps (predominately a 254 nm wavelength component from both lamps 10, 12 plus a 185 nm wavelength component from quartz VUV lamp 10) also interacts directly with pathogens in air flowing through chamber 11 killing many pathogens, or rendering them incapable of reproduction, so as to provide a sterilizing effect. Ultraviolet radiation within chamber 11 will also tend to raise excitation states of pyrogens and other substances in air flowing through chamber 11 so as to promote other reactions between such excited constituents and ozone or atomic oxygen. These direct interactions between ultraviolet radiation and pathogens, pyrogens, or other substances in air flowing through chamber 11 occur only while air and contaminants are inside chamber 11 and thus exposed directly to ultraviolet radiation from lamps 10, 12. However, excited states resulting from direct ultraviolet radiation may continue to promote reactions even after exposed air has exited unit 4.

In yet a third type of interaction, 254 nm wavelength ultraviolet radiation from both lamps 10, 12 interacts with ozone molecules, tending to break bonds within ozone molecules, thereby causing some ozone created within chamber 11 to be immediately disassociated back into freed oxygen atoms and diatomic oxygen molecules. This interaction of ozone molecules with 254 nm wavelength ultraviolet radiation results in a reduction of concentration of ozone exiting air purification unit 4, but also causes additional reactivity and reactions in air and contaminants while in chamber 11. These additional reactions contribute to a fourth type of beneficial interaction as described below.

In this a fourth type of interaction, oxygen atoms developed by disassociation of diatomic oxygen by 185 nm wavelength ultraviolet light from quartz VUV lamp 10, in conjunction with other oxygen atoms freed in disassociation and breakdown of ozone molecules by 254 nm wavelength ultraviolet radiation from both lamps 10, 12, and ozone molecules themselves react with other molecules and substances in air. These other substances may include water vapor, methane or other hydrocarbons or organic compounds, halogen molecules or compounds, metallic particles or compounds, and the like so as to create ions or other molecular compounds, collectively referred to as ozonites. Ozonites resulting from interactions of ozone with hydrocarbons and other organic compounds, or with metallic compounds, are generally less reactive than ozone, but are generally still reactive enough to continue to react, generally via oxidative reactions, with other contaminants in air, and thereby continue and sustain purifying reactions at greater distances, and at longer time, than is achievable by actions of generally more reactive, but shorter lived, ozone molecules. As noted earlier, ozonites resulting from interactions of ozone with water vapor (leading to creation of hydroxyl radicals) or with halogens or halogen compounds are generally more reactive than ozone itself, and such ozonites have an ability to oxidize some contaminants that are less likely to be oxidized by ozone.

Referring again to FIG. 5, and as noted above, multiple modes of operation are possible and desirable for some applications. In a relatively simple embodiment illustrated in FIG. 1 through FIG. 4, at least three modes of operation are supported by various configurations of control switches and other components. In an embodiment illustrated in FIG. 5, a master on-off switch 22 controls power to other components of unit 4. Master on-off switch 22 may be a fused double-pole, single-throw type as illustrated in FIG. 5, or may be a simpler, single-pole, single-throw switch, preferably in a power side of a line. Other types of switches as indicated by safety, electrical code, and other considerations may also be used. Components powered directly from master switch 22 include a ballast 16 for a germicidal UV-C lamp 12, an intake fan 20, and an ozone/timer select switch 24, which may be of a single-pole double-throw type or other type. Depending upon its position, ozone/timer switch 24 allows power to be routed directly to ballast 14 for a quartz VUV lamp 10 or routed through a timer 30, which then controls flow of power to ballast 14 for quartz VUV lamp 10. Timer 30 may be of a simple 24-hour cycle electromechanical type, similar to those commonly sold to control lights in a house when occupants are away, and which may use push-pins or another user-selectable mechanism for selection of ON and OFF periods, or timer 30 may be of a more complex electronic type, using push-buttons and an electronic display, or another type of user interface, for selection of timing of ON and OFF intervals. Timer 30 may typically be configured to provide power to a ballast 14 for a quartz ultraviolet lamp 10 in 15 minute intervals one or more times per day.

When operated in a "CONTINUOUS OZONE OUTPUT" mode as discussed above, ozone/timer switch 24 is set to "OZONE" position. Then master switch 22 is switched ON, providing power directly to an intake fan 20 and to a ballast 16 for a germicidal UV-C lamp 12 and to ozone/timer switch 24. For this "CONTINUOUS OZONE OUTPUT" mode, with ozone/timer switch 24 set to "OZONE" position, continuous power is provided to a ballast 14 for a quartz VUV ozone generating lamp 10 and an exhaust fan 18 so that all reactions described above for this mode may take place. Unit 4 should generally be used in a "CONTINUOUS OZONE OUTPUT" mode only when an area to be treated is not occupied by humans, pets, or other desired organisms that could be harmed or irritated by higher concentrations of ozone that unit 4 is capable of generating in an enclosed area when run in "CONTINUOUS OZONE OUTPUT" mode.

When used in a typical household environment, for example, unit 4 may be operated in a "TIMED OZONE OUTPUT" mode and may be placed in front of an intake air duct grill for a heating and air conditioning system (HACS) where a HACS circulation fan has been set to run continuously. In this application, ozone/timer switch 24 is set to "TIMER" position so that when power switch 22 is switched on, power is provided to intake fan 20, ballast 16 for UV-C lamp 12, and to ozone/timer switch 24 as described earlier. However, in this mode, ozone/timer switch 24 routes power to timer 30. Timer 30 could be configured via push pins, for example, so that quartz VUV lamp 10 is turned on for two consecutive 15 minute intervals shortly after household occupants leave the house for work or other daily activities, and timer 30 could also be configured to activate quartz ultraviolet lamp 10 for one or two additional 15 minute intervals ending shortly before occupants return to the house later in the day. In this configuration and operational mode, unit 4 would provide a continuous germicidal action for household air, and would provide two brief shock treatments per day using higher ozone concentrations to help oxidize contaminants and provide additional air purification action. When quartz VUV ozone generating lamp 10 is powered ON by timer 30, all interactions discussed above for "CONTINUOUS OZONE OUTPUT" mode may take place; thus producing ozone and ozonites in addition to providing germicidal action. Ozonites produced during these shock treatments will have lasting benefits in household air even after ozone generation lamp 10 is switched off.

In order to obtain germicidal or ozone reducing benefits of a germicidal UV-C lamp alone in treating air flowing through unit 4, unit 4 is operated in a "GERMICIDAL ONLY" mode. In this mode, ozone/timer switch 24 is set to "TIMER" position, but push-pins on electromechanical timer 30 of our example are all pulled out so that timer 30 never provides power to quartz VUV lamp 10. When master switch 22 is switched ON, power is provided to intake fan 18, ballast 16 for germicidal lamp 12, and to ozone/timer switch 24. However, because timer 30, when configured for this mode, does not provide power to ballast 14 for VUV lamp 10, only germicidal lamp 12 is energized, providing germicidal action and extinction of any residual ozone in air flowing through unit 4, which may lead to secondary production of a few ozonites, but no new ozone is produced by VUV action.

Figure 6:
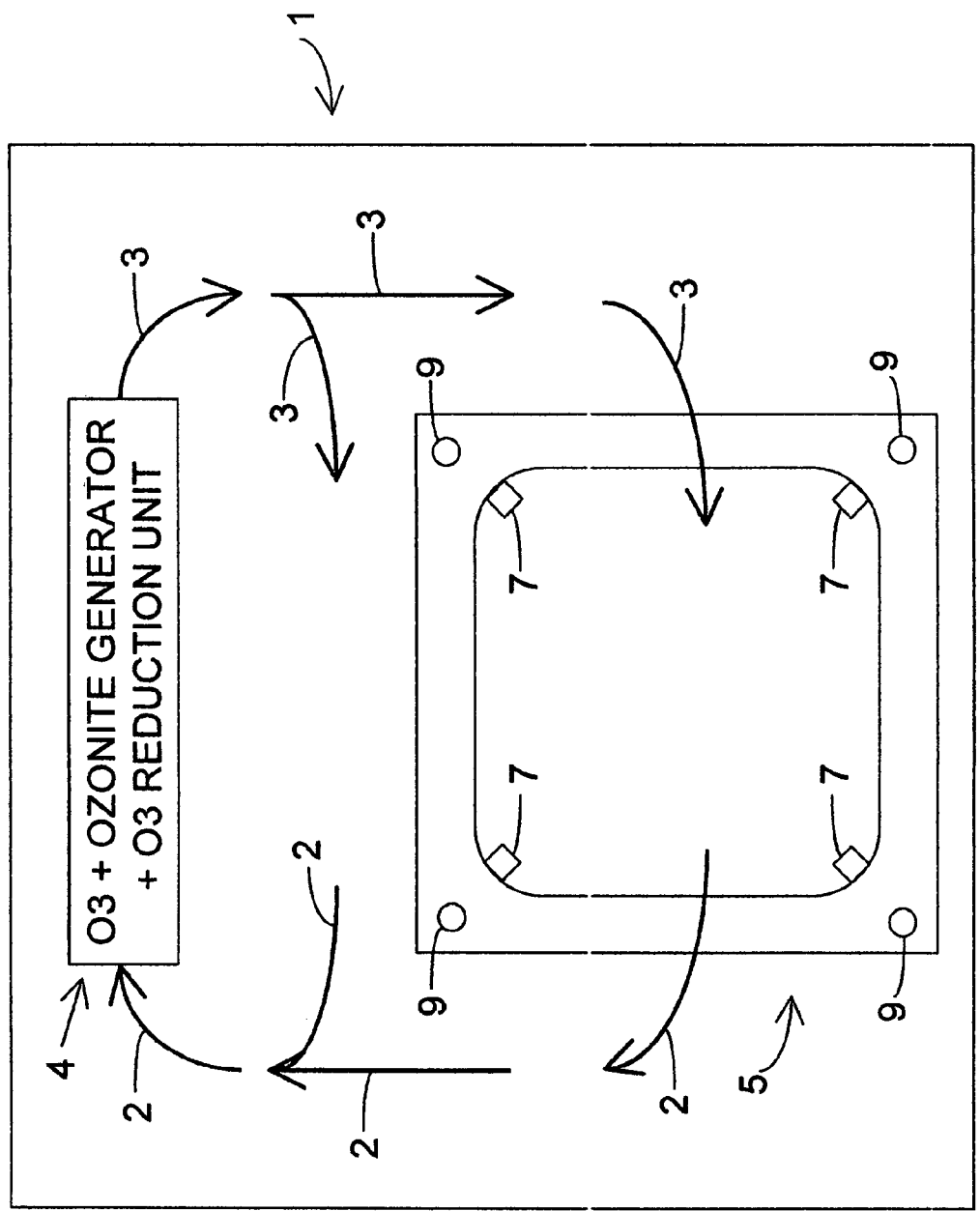
FIG. 6 is a schematic illustrating how an embodiment of the instant invention may be used in conjunction with a sanitized jetted bathing facility to remove ozone from ambient air occupied by bathers.

Because ozone reduction capability of a "GERMICIDAL ONLY" mode of the embodiment described in FIG. 1 through FIG. 5, or other embodiments such as those shown later herein offering a similar mode, an embodiment such as shown in unit 4 is useful in a standalone application or in an integrated mode in applications where removal, or reduction in concentration, of ozone is desired. One example of such use is illustrated in FIG. 6 wherein a unit 4 is shown being used with a sanitized jetted bathing facility, such as disclosed in Applicant's U.S. Pat. No. 6,405,387. In this application, ozone that may be released into ambient air from water discharge jets 7 or other openings due to use of ozone in sanitizing water, plumbing, or other fixtures, as disclosed in aforementioned patent, in an enclosed or partially enclosed area 1 associated with a spa, whirlpool bath, or similar facility, may be removed by an ozone extinction capability of an embodiment of the instant invention similar to unit 4 disclosed above. Alternately, one or more lamps, such as a germicidal UV-C lamp discussed herein, capable of emitting an ultraviolet wavelength around 254 nm suitable for causing breakdown of ozone molecules, without emitting shorter wavelengths leading to breakdown of diatomic oxygen (leading to creation of ozone) could be added to ozone generators used for applications disclosed in Applicant's U.S. Pat. No. 6,405,387, with additional operational modes, which should be evident from disclosures herein, designed to promote generation of ozonites or to remove ozone from air in plumbing as well as from room air drawn in through air vents and valves 9.

FIG. 6 also provides a convenient illustration to disclose another concept and feature achievable in certain applications and embodiments of the instant invention, namely achievement of a closed-loop system wherein output air 3 from an embodiment of the instant invention such as unit 4 flows throughout an enclosed or partially enclosed space, which may be a room, an entire house, a tent, or other such space, and is then re-circulated so as to flow through an ozone generation and destruction unit 4 multiple times. By providing for multiple passes through a unit 4, with controls set to an operating mode as disclosed herein for such a unit, effects of a selected operating mode are generally reinforced or amplified, leading, for example, in different modes, to higher concentrations of ozone and ozonites, or in other modes, to more complete destruction and removal of ozone, from ambient air. For example, a "MAXIMUM OZONE OUTPUT" mode may be selected just after use of a spa or jetted tub, when an enclosure 1 of a spa or jetted tub will not be occupied for a time, so that combined ozone generating capabilities of a standalone unit 4 and an ozone generator used with a spa or jetted tub as disclosed in Applicant's U.S. Pat. No. 6,405,387 are combined to provide a high ozone concentration "shock" treatment within an overall enclosure 1 to promote destruction of bio-slime, spores of molds and fungi, and other pathogens, which may be in more susceptible states due to exposure to moisture and high levels of water vapor during use of a spa or jetted tub 5. In addition, presence of higher levels of water vapor in ambient air during such times may lead to generation of more reactive hydroxyl radicals, as disclosed earlier, which may be more effective in destruction of pathogens and pyrogens in enclosed area 1. In an application as illustrated in FIG. 6, an additional re-circulation loop may be created when ozonated room air 3 is drawn into air valves 9 of a spa or jetted tub, or into other vents, used to provide air to one or more ozone generators used to treat bio-slime and other contaminants in plumbing and other fixtures of a spa or jetted tub 5. Re-circulation of treated air in one or more closed loops may, in general, be used to reinforce or enhance effects provided by any given operational mode of an embodiment of the instant invention.

Continuing with FIG. 6, it may be seen that a unit 4 may also be used to remove ozone from air within enclosed space 1 by selection of a "GERMICIDAL ONLY" or similar operating mode wherein one or more germicidal lamps producing UV-C radiation as described earlier herein are energized but ozone generating VUV lamps are not energized. Such an application and mode may be useful in rapidly reducing ozone concentrations to levels comfortable for human occupation of an enclosed space 1 after an ozone "shock" treatment as described above, or in controlling ozone released to ambient air during use of an embodiment of the instant invention disclosed in Applicant's U.S. Pat. No. 6,405,387.

Figure 6A:
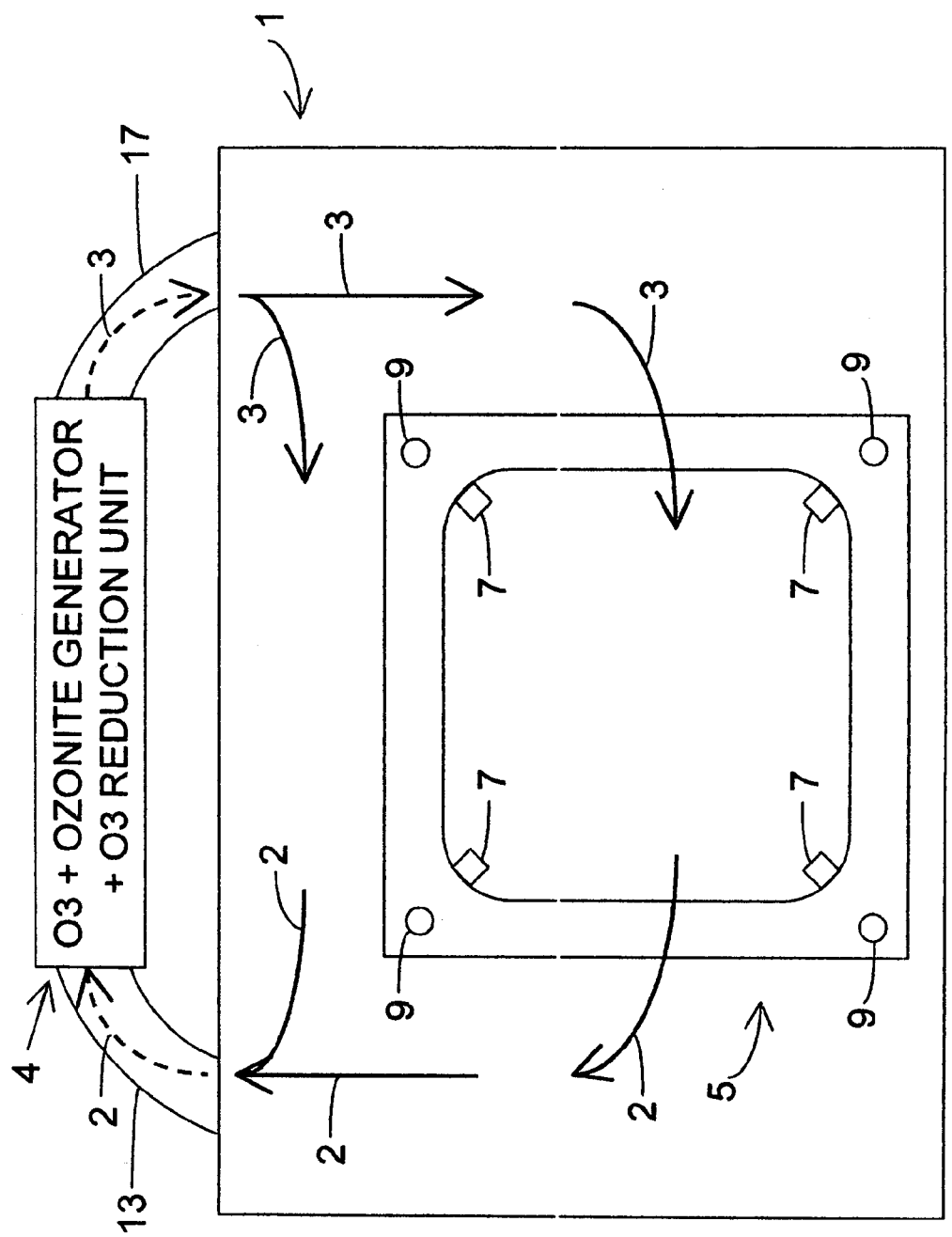
FIG. 6A is a schematic illustrating how an embodiment of the instant invention may be connected to an area to be treated by use of air ducts.

FIG. 6A illustrates how an embodiment of an ozone and ozonites generator of the instant invention may be located outside of a generally enclosed area to be treated, but connected to an area to be treated by at least one intake air duct 13 and at least one exhaust air duct 17. An embodiment such as unit 4, other embodiments such as disclosed later herein, or alternate embodiments made evident from disclosures herein may be connected to a generally enclosed area 1 as illustrated in FIG. 6A. An enclosed area 1 to be treated may be a spa, as illustrated, or virtually any other generally enclosed volume, such as a grain elevator or storage bin or other container of agricultural products, laundry hampers or clothes bins, outdoor portable toilets or outhouses, or containers used specifically for treating contaminated objects or substances such as mildewed books, grain contaminated with fungal, bacterial, or other organisms, and the like. Such containers may include open mesh shelves to promote flow of air containing ozone and ozonites around objects being treated, or through porous objects such as linens or clothes. Any of the operational modes may evident from disclosures herein may be used in a configuration as illustrated in FIG. 6A. In a further expansion of use of embodiments of the instant invention external to, but connected to and communicating with, an area to be treated, it will be evident to those skilled in the arts of air movement that one or more embodiments of the instant invention may be connected to a plurality of enclosed volumes to be treated by use of additional ducts and including use of Y's, T's, or other fittings, including, for example, use of pneumatic or electrically controlled dampers to switch intake and exhaust flows among different enclosed volumes at different times to permit desired concentrations to be more readily controlled in each volume. It should be evident also, that benefits may be obtained from open loop operation, wherein exhaust air from an air treatment unit, such as unit 4, of the instant invention is directed into an enclosed volume, but displaced air is released from the volume being treated without being recirculated through the air treatement unit. Normally, however, greater benefits may be realized from closed loop operation, wherein exhaust air 3 containing ozone and ozonites from an ozone and ozonites generator (e.g., unit 4) is directed into an enclosed volume 1 and allowed to circulate throughout the enclosed volume 1, providing benefits of sterilization and purification noted earlier herein, and then recirculated as intake air 2 back through the air treatment unit, wherein other contaminants that become mixed in the air flow are treated, and concentrations of ozone and ozonites are enhanced in air 3 returned to the enclosed volume 1. In this and other applications disclosed herein, an ozone and ozonites generator may be operated, for example, in a ozone and ozonites generation mode for a period of time generally sufficient to allow a desired maximum concentration to be achieved in an enclosed area being treated. The interval of time for such a mode may be selected by a user via a timer of a control system for the ozone and ozonites generator 4. Alternatively, in embodiments containing an ozone detector in an intake air flow, or communicating with a ozone detector placed in an enclosed area being treated, a user may select a maximum ozone level to be provided in the enclosed area, and the ozone and ozonites generator may be operated in an ozone generation mode until a desired ozone concentration is reached in the enclosed area, after which the ozone generation mode of the air treatment unit may be terminated. Either immediately, or after an delay selected by a user, an ozone reduction mode of an ozone and ozonites generator 4 may be selected and activated to reduce ozone concentrations to levels safe for human occupancy or to some other desired concentration. The duration of operation of the ozone and ozonites generator and ozone reduction unit in the ozone reduction mode may be determined by use of a timer or, in embodiments equipped with or communicating with an ozone detector, by use of a control signal indicating the desired reduced concentration of ozone in the enclosed volume has been achieved. It should be evident that similar modes of operation may be used irrespective of whether an ozone and ozonites generator of the instant invention is located within, or external and connected to, a generally enclosed volume to be treated.

As was noted earlier, a "MAXIMUM OZONE OUTPUT" mode, wherein VUV lamp 10 is energized, but ozone destroying UV-C lamp 12 is OFF, may be desirable for some applications. Such a mode may be added to basic unit 4 as disclosed in FIG. 1 through FIG. 5. One example of how such a mode may be added is illustrated in FIG. 7, which shows an embodiment similar to that of FIG. 5 except for addition of another switch 36 which provides an ability for a user to switch OFF power to ballast 16 for UV-C lamp 12. Such a switch 36 may be a simple single-pole single-throw switch labeled, for example, as a UV-C LAMP ON/OFF switch, or labeled with open position indicated as MAX OZONE and closed position labeled as CONTINUOUS OZONE/OZONITE. Operation and effects of other components illustrated in FIG. 7 are otherwise similar to that described for FIG. 5.

Figure 8:
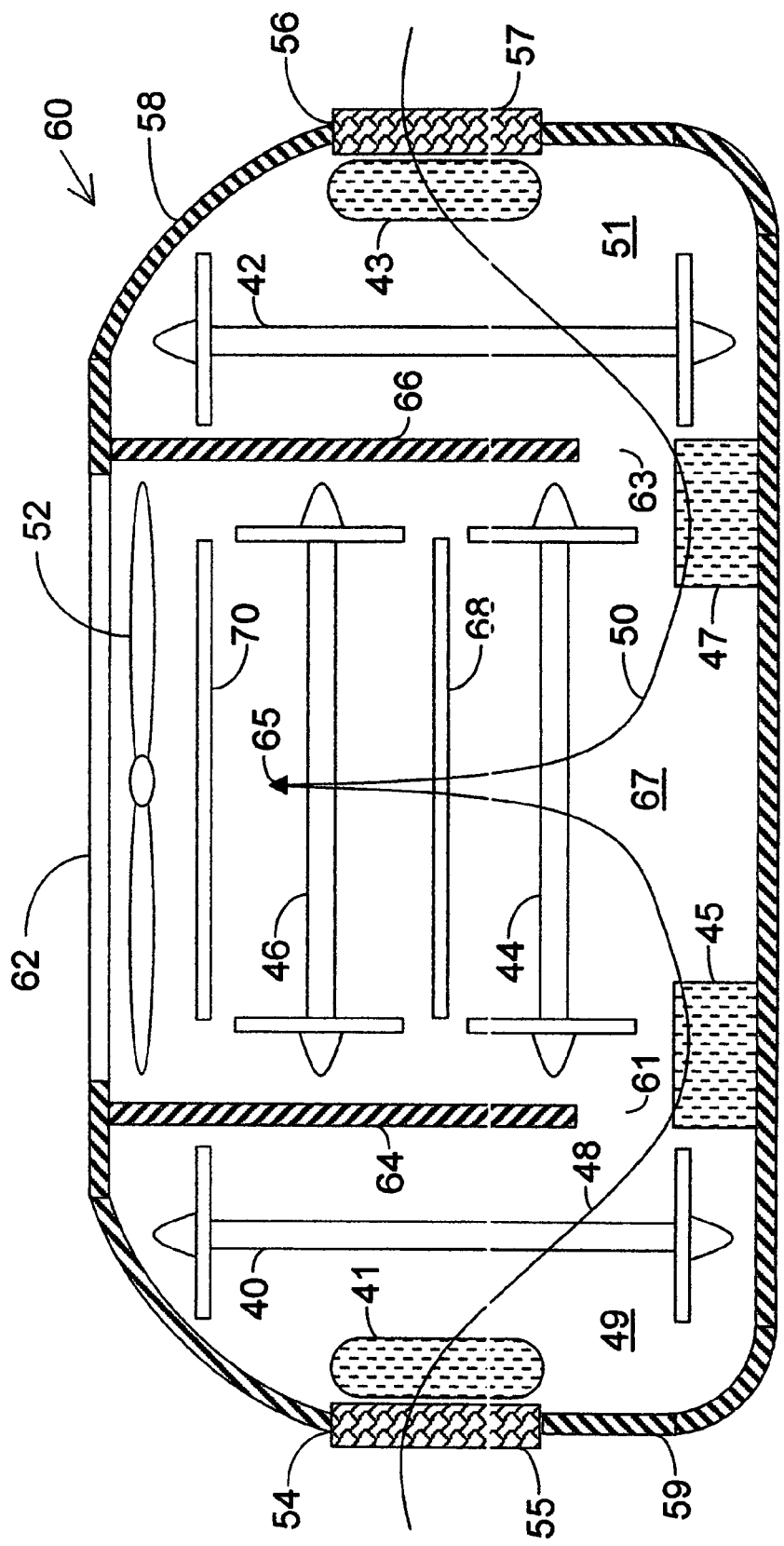
FIG. 8 is a diagrammatic illustration showing particulars of construction of another embodiment of the instant invention.

By way of illustration of how some features and innovations described heretofore in this application may be implemented, and benefits realized, in other embodiments of the instant invention, reference is made to FIG. 8. Here, unit 60 shown in FIG. 8 is another primary embodiment of the instant invention. In this embodiment, unit 60 constitutes a sanitizer/sterilizer and includes a housing 58 having entrances 54 and 56 covered by filters 55 and 57, respectively, to catch at least some airborne particles that would otherwise enter housing 58. A fan 52 draws air into housing 58 through filters 55, 57 and creates air streams indicated by arrows 48 and 50. After passing through entrances 54, 56 and filters 55, 57, air in streams 48, 50 enters regions, or chambers, 49 and 51, in which sources 40 and 42 of VUV radiation are located. In a primary or alternate embodiment, either or both sets 41, 43 or 45, 47 of optional humidifiers or other reagent injection devices may be added within a general path of air streams 48, 50, with either set 41, 43 or 45, 47 creating different effects in performance and actions of overall unit 60 based upon their respective locations within air stream 48, 50 relative to other components, and particularly relative to locations of VUV sources 40, 42, as explained later. Humidification or reagent injection devices may simply be evaporative, such as Seltzer pads or other types of wicks, or may make use of various atomization techniques, including use of ultrasonic action or use of high-pressure atomization nozzles. Humidification or reagent injection devices may include reservoirs that must be refilled periodically, or they may make use of connections to external sources of water or other reagents so as to minimize maintenance and servicing. Techniques used for humidification or reagent injection should avoid contamination of surfaces of VUV or UV-C tubes with mist or droplets that could lead to deposits of residue on such tubes, which may interfere with transmission of ultraviolet radiation from such tubes. Exterior walls 58 and 59 of chambers 49 and 51 as well as interior walls 64 and 66 and filters 55 and 57 of those chambers 49, 51 are opaque to ultraviolet radiation so that none will escape into any other part of unit 60 or out to surrounding space. In this embodiment only one VUV source 40, 42 is shown athwart each entrance chamber 49, 51, respectively, although unit 60 may have multiple VUV sources in each entrance chamber if more intense radiation is desired. Radiation emitted by each VUV source 40 and 42 interacts with oxygen, pathogens, pyrogens, and other substances in incoming air streams 48, 50, initiating those reactions discussed earlier. When optional humidification or reagent injection devices 41, 43 are used, air flowing past VUV tubes 40, 42 will contain enhanced levels of water vapor or other reagents, leading to additional reactions and enhanced concentrations of different types of ozonites, for different purposes, as discussed earlier.

While arrows indicating a flow make it appear that air streams 48, 50 flow smoothly through chambers 49, 51, this is not actually the case. It is desirable that air circulate somewhat turbulently in chambers 49, 51 to get sufficient exposure to VUV radiation for reasons discussed earlier herein. Air does not linger in entrance chambers 49, 51; in a relatively short time, air in streams 48, 50 flows through openings 61 and 63 to converge into a single air stream 65 in a central region, or chamber, 67 in which movement of air may also be turbulent to obtain advantages and effects discussed earlier. In embodiments where optional humidification or reagent injection devices 45, 47 are added and used, additional water vapor or other reagents may be added to air streams 48, 50 at this stage, with a purpose of further modifying creation of ozonites and controlling air chemistry taking place within device 60 or subsequently within area being treated by use of device 60. Addition of humidity to exiting air will tend to promote expansion and blooming of fungal spores, rendering them more susceptible to reaction with and neutralization by ozone also generated and emitted by device 60 in certain modes of operation. Central chamber 67 in this embodiment contains two UV-C sources 44 and 46. UV-C radiation from these sources destroy some ozone created by VUV lamps 40, 42 and contribute to generation of ozonites, in addition to providing a sterilizing action, as discussed earlier herein. Reflectors 68, 70 may be placed between UV-C sources 44, 46 and an exit 62 to increase exposure of air stream 65 to UV-C radiation in order to further reduce or eliminate residual ozone and react with contaminants. Reflection of UV-C radiation makes it possible to strike and destroy those pathogens within its destructive capacity and which would otherwise be shadowed from radiation radiated directly from UV-C sources 44, 46. Reflectors also help prevent UV-C radiation from sources 44, 46 from escaping through exit 62.

Figure 9:
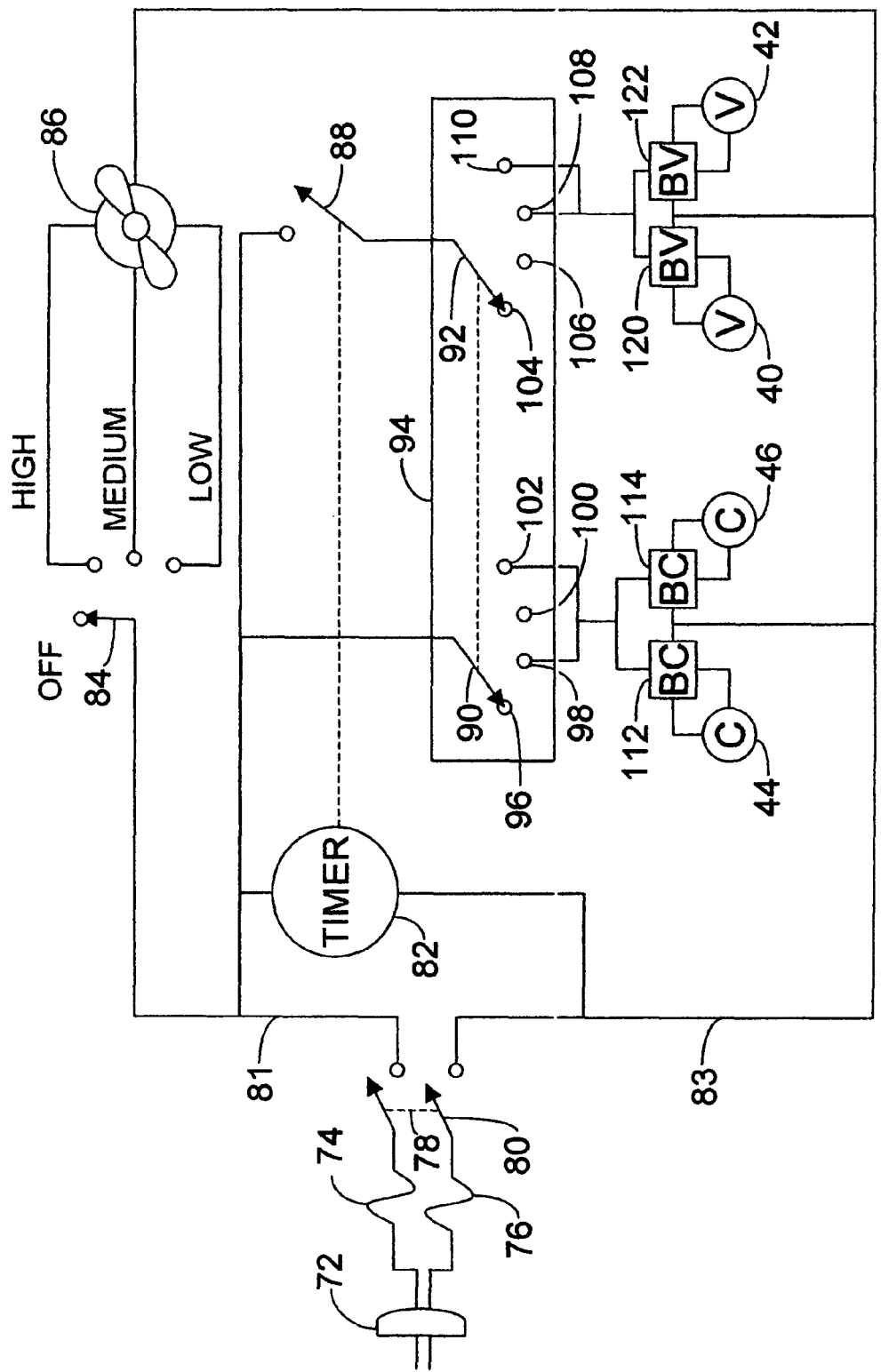
FIG. 9 is a block diagram of a control system of the instant invention.

FIG. 9 is a schematic diagram of a circuit which may be used to control unit 60. This embodiment is set up to operate from standard 110 volts AC, and it includes a plug 72 pluggable into a standard AC outlet. Fuses 74 and 76 are connected in series with each power line along with one pole of a two-pole single-throw switch 78. One line 83 to the right of switch 78 may be considered a common wire and the other line 81 may be a hot wire. A timer 82 connected directly to lines 81 and 83 can be energized when switch 78 is closed, and a switch 88 connected electrically to line 81 and mechanically to timer 82 may be opened after a length of time determined by a setting programmed into timer 82 by a user of unit 60.

A manually controlled four-position switch 84 connects line 81 to fan motor 86 for fan 52 in FIG. 8. The arm of switch 84 is shown engaging a first contact, to which nothing is connected. In this position, switch 84 is in an OFF position in which fan motor 86 is not energized. Other contacts of switch 84 are marked, successively, HIGH, MEDIUM, and LOW and are connected to terminals on fan motor 86 to control its speed to be high, medium, or low according to a number of cubic feet per minute of air considered to be necessary. In general, a larger space to be treated requires a higher fan speed. Fan motor 86 has another terminal connected to common line 83 to complete a power circuit for fan motor 86.

Unit 60 also includes a two-layer four-pole switch 94 to control VUV sources 40 and 42 and UV-C sources 44 and 46. A first layer of switch 94 has an arm 90 connected directly to line 81 and is shown in its first, or "off," position engaging an open contact 96. A second contact 98 that arm 90 can engage is connected to one end of a parallel circuit comprising two ballasts 112 and 114 for two UV-C lamps 44 and 46, respectively. An other end of each parallel circuit is connected to common line 83. A third contact 100 that arm 90 can engage is another open-circuit position, and a fourth contact 102 is connected directly to a second contact 98 and, therefore, to one end of a parallel circuit comprising ballasts 112, 114 for UV-C lamps 44, 46. Switch 88 is connected in series between line 81 and arm 92 of a second layer of switch 94. This arm, which is ganged with arm 90, can also be set to engage any one of four contacts: an open contact 104 in a first, or "off" position; a second contact 106 to which nothing is connected; a third contact 108; or a fourth contact 110. Third and fourth contacts, 108 and 110, respectively, are short-circuited together and connected to one end of another parallel circuit comprising ballast 120 for VUV lamp 40 in one leg and ballast 122 for VUV lamp 42 in another leg. An other end of each leg of a parallel circuit thus created is connected to common line 83.

Unit 60 can be operated in any of several modes of operation determined by a setting of switch 94. In each mode, switch 84 is required to be changed from an OFF position in which it is shown to another position in order to set a stream of air in motion through unit 60. Speed selection for fan motor 86 depends on an amount of air that must be moved and a velocity at which it is to be moved.

In a first mode, switch 94 is set to its second position, in which arm 90 engages contact 98 and arm 92 engages open contact 106. In this position, current can pass through arm 90 to turn on UV-C sources 44, 46. At the same time, no current will flow through arm 92 and open contact 106, even if switch 88 controlled by timer 82 is closed. This mode provides sterilization by ultraviolet radiation of air passing through unit 60 in a manner discussed earlier. Additionally, if there is any ozone in air being brought into unit 60 by fan 52 in this mode, it will be destroyed by UV-C irradiation inside unit 60.

In a second mode, arms 90 and 92 are set to their third positions to engage contacts 100 and 108, respectively. Contact 100 is not connected to anything, so no current will flow through arm 90, but contact 108 is connected to a parallel circuit comprising ballasts 120 and 122 for VUV sources 40 and 42. If switch 88 is set in its closed position by timer 82, current can flow through contact 108 and ballasts 120, 122 for VUV sources 40, 42, causing them to generate ozone from molecular oxygen drawn into entrance chambers 49 and 51. Timer 82 is convenient for controlling operation of VUV sources 40 and 42 so that they will generate ozone only when it is safe to do so, i.e., when people are not in, or are only briefly in, a space to be treated. If no one is to be in a treated space for several hours, such as all night, timer 82 can be set to allow VUV sources 40, 42 to be operated for most of that time and to be switched off long enough at the end of that time to allow all ozone to disintegrate. However, if it is necessary to generate ozone when people are in a room being treated, timer 82 may be set to allow switch 88 to be closed and ozone to be generated for repeated short intervals, such as a few minutes each hour.

As ozone from VUV sources 40 and 42 pervades a room, it is capable of destroying odors, pyrogens, and pathogens including not only bacteria and viruses but also fungi, molds, and alcohol that might be present. In addition, ozone renders reactive metal particles in air inert by oxidizing them so that they become incapable of reacting with other materials. In effect, oxidation of these contaminants by ozonator unit 60 burns them so that they are no longer toxic.

In a third mode, switch 88 is closed and arms 90 and 92 are set in their fourth positions in which they engage contacts 102 and 110, respectively. This energizes UV-C sources 44 and 46 as well as VUV sources 40 and 42. VUV radiation from sources 40 and 42 generate ozone from molecular oxygen drawn into entrance chambers 49 and 51, and this ozone immediately begins to sterilize and purify that air. At the same time, there is some sterilization of that air directly by exposure to VUV radiation. As air containing ozone is drawn into central chamber 67 by fan 52, ozone remaining in that air continues to attack contaminants, and this effect is enhanced in central chamber 67 by operation of UV-C sources 44 and 46 that cause ozone to disassociate and be in a highly reactive state that enhances its ability to react with contaminants that have not been reacted with up to that time. Thus, although UV-C radiation from sources 44, 46 would seem to have an undesirable effect by initiating return from ozone to molecular oxygen, this return causes extra oxygen atoms to pass through a state in which they are even more reactive with contaminants than they would be if they continued to be parts of ozone molecules up to the time they encountered contaminant particles.

Sanitization of an unoccupied room by operation of unit 60 in a third mode may be further controlled by operation of fan switch 84 and timer 82 to cause an unoccupied room to be sanitized by high levels of ozone initially and then returned either to a condition in which there are still acceptably low levels of ozone or to a condition in which there is complete elimination of ozone.

Some contaminants that ozone can react with are toxic if they are inhaled, and reaction with such sources of irritation is one important benefit of unit 60. For one thing, ozone breaks up or modifies long chains of very complex molecules, such as odor from tobacco smoke, which is a long, organic chain. Ozone will disrupt that chain, thereby eliminating its odor. Tobacco smoke includes a gummy tar with a nicotine virus and is, therefore, particularly undesirable in a ventilating system of a car. All these things, which can be irritants if breathed heavily for awhile, are destroyed by ozone.

An ability of ozone to break down long, organic chains can also be very useful in eliminating other odors that accumulate in heating and air conditioning systems of automobiles. Cars sometimes get very hot and at other times very cold, and since they are outdoors much of the time, they pick up a lot of contaminants. Since an air circulating system in a car typically has no filter in it, these contaminants stick to interior wall surfaces in an air circulation system and need to be eliminated. Even if it is not desirable to destroy all contaminants on walls of ventilating systems continually, it may be very desirable to have a capacity to do so at specific times. Putting a unit 60 in an automobile, setting a unit 60 to generate ozone, and turning on all air conditioning and circulating equipment, causes ozone to go through all little radiators and other components of a ventilating system and destroy smoke molecules, nicotine viruses, and other contaminants adhering to walls of a ventilating system.

Another advantage of ozone is that it reacts with halogen molecules by replacing halogens with oxygen, which essentially changes a molecule that would be toxic into one that is nontoxic. So, almost across the board, ozone converts toxic pyrogens to non-toxic waste.

Figure 10:
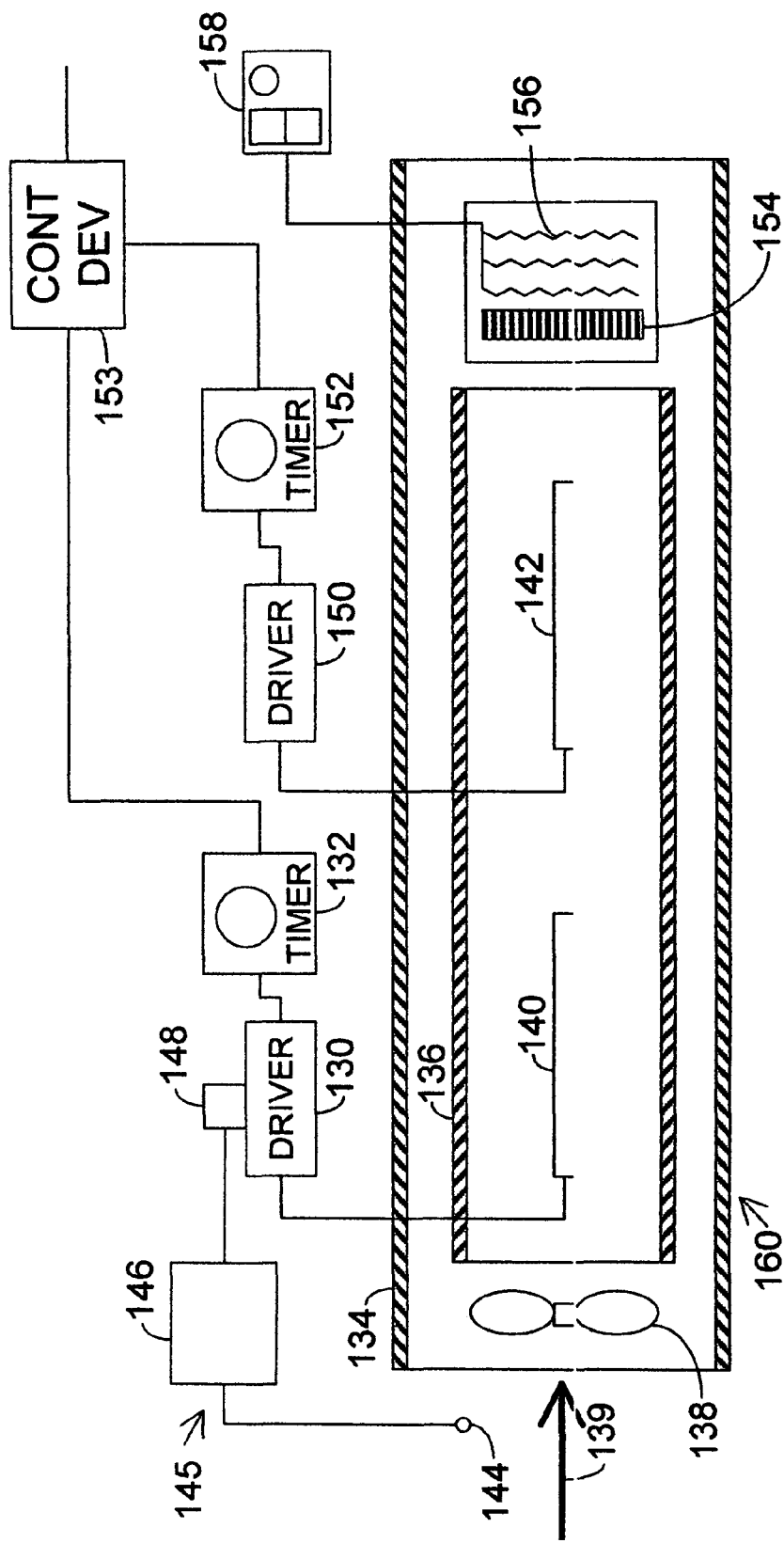
FIG. 10 is a partially diagrammatic partially block diagram showing another embodiment of the instant invention.

FIG. 10 is a schematic representation of a unit 160 that constitutes another embodiment of the present invention. The basic structure of this unit is a duct 134 opened at both ends. A fan 138, shown in this embodiment as being located at an input end of duct 134, produces an air stream 139 that flows into that end of duct 134 and on through a space of annular cross section between an elongated lamp 140 and a tubular reflector 136. Lamp 140 is a source of VUV radiation and reflector 136 is formed either on an inner surface of duct 134 or as a separate tubular member within duct 134. Electric current to energize VUV source 140 to produce ozone is derived through a lamp driver 130 controlled by a timer 132. As previously described in connection with the embodiment in FIG. 8, a timer such as timer 132 can be set to operate VUV source 140 continuously for a selected period of time or intermittently according to an amount of ozone required to react with contaminants to sanitize air stream 139 and a room within which unit 160 is located. Pathogens that can be destroyed by ultraviolet radiation passing through air stream 139 are further attacked by VUV directly. Lamp driver 130 is also connected to an ozone sensor 145 that includes both an ozone sensitive component 144 and a control unit 146. Ozone sensor 145 is capable of measuring ozone in air re-entering unit 160 after having circulated through a room in which unit 160 is located. Sensor 145 is connected to lamp driver 130 via a control box 148 to control operation of lamp driver 130 to cause VUV source 140 to continue to produce ozone until a desired ozone concentration in the room, as measured by sensor 145 in air that finds its way back to an input end of unit 160, is obtained.

Unit 160 also includes a second lamp 142 that constitutes a source of UV-C radiation downstream of VUV source 140. UV-C 142 source derives its operating current from a second lamp driver 150 controlled by a second timer 152. Both timers 132 and 152 are connected to an ozone-measuring and control device 153. UV-C source 142 disassociates ozone in air stream 139 flowing past source 142, thereby accelerating reaction of resulting atomic oxygen with pathogens and pyrogens in air stream 139, promoting generation of ozonites, and further sterilizing and sanitizing air in unit 160. In so doing, UV-C from source 142 speeds up return of a room in which unit 160 is operating to an ozone-free condition, reducing a time interval within which ozone may be uncomfortable to humans and pets. This reduces time humans would have to remain out of the room from time required if ozone molecules only disassociated at their normal spontaneous breakdown rate. This arrangement also promotes generation of ozonites with advantages discussed earlier herein. UV-C radiation from source 142 also assists in destroying pathogens, both by direct impingement on those pathogens and by reflected impingement on them from reflector 136.

An organic or highly reactive filter 154 is included in an exit end of unit 160 to trap contaminants and to assist in destroying residual ozone molecules remaining in air stream 139 as it leaves unit 160. This has two effects; a first to sterilize filter 154 by reaction of ozone and atomic oxygen with trapped contaminants, thereby making filter 154 more reactive with respect to contaminants arriving later, and a second effect to destroy more of residual ozone in air stream 139. Filter 154 is not needed under all of modes of operation of unit 160 and may, therefore, be removable. A heater 156 associated with filter 154 can be used to increase rate of destruction of ozone by raising temperature of filter 154.

A degree of sterilization and sanitation within air stream 139 as it exits from duct 134 and amounts of ozone and ozonites within an exiting air stream can be controlled in several ways. One way is to adjust speed of fan 138 to change speed of air stream 139. Another way is to use ozone sensor 145 to make lamp driver 130 inoperative when concentration of ozone in air returning to unit 160 gets up to a selected level. Yet another way is to use control device 153 to control operation of VUV source 140 and UV-C source 142. Control device 153 may control timer 132 to determine timing of intervals when VUV source 140 is energized to generate ozone, and can control timer 152 to determine when UV-C source 142 is energized to destroy ozone. Sterilization and sanitation of air stream 139 can also be controlled by means of a heater control 158 to which heater 156 is connected and which sets intensity of heat and times heater 156 is switched ON.

Using these controls, unit 160 can operate in several different modes. In one mode, unit 160 can provide a high level of ozone in air stream 139 to sanitize air in a room by fully energizing fan 138 and VUV source 140, with filter 154 removed from air stream 139. VUV source 140 is controlled by timer 132 so that system 160 can operate in this mode only during intervals when people are not in, or are only briefly in, a room being sanitized. As a further safety measure, timer 132 can be set to allow operation of VUV source 140 for only brief intervals, for example, fifteen minutes at a time.

A second operating mode is to provide sterilization of air stream 139 in unit 160 and to remove residual ozone from air stream 139 without generating any further ozone. In this mode, only fan 138 and UV-C source 142 are switched on. Filter 154 may be left in place.

A third mode of operation provides maximum sterilization and sanitation within unit 160 and low levels of ozone output. In this mode, filter 154 is left in place, and fan 138, VUV source 140, UV-C source 142, and heater 156 are operated at maximum output. If a level of ozone is to be automatically controlled to a low level, ozone level sensor 145 and control 158 can be used to cycle intensity of VUV source 140 and filter heater 156.

A fourth mode of operation may be used to allow an unoccupied room to be sanitized by a high level ozone initially by having both VUV and UV-C sources 140 and 142, respectively, switched ON and speed of fan 138 and heater 156 operated at their highest respective settings. This condition is cycled by timers 132 and 152 to return to a mode producing lower levels of ozone, or to a mode causing complete elimination of ozone. Maximum sterilization is provided with ozone levels controlled by ozone level sensor 145.

Figure 11:
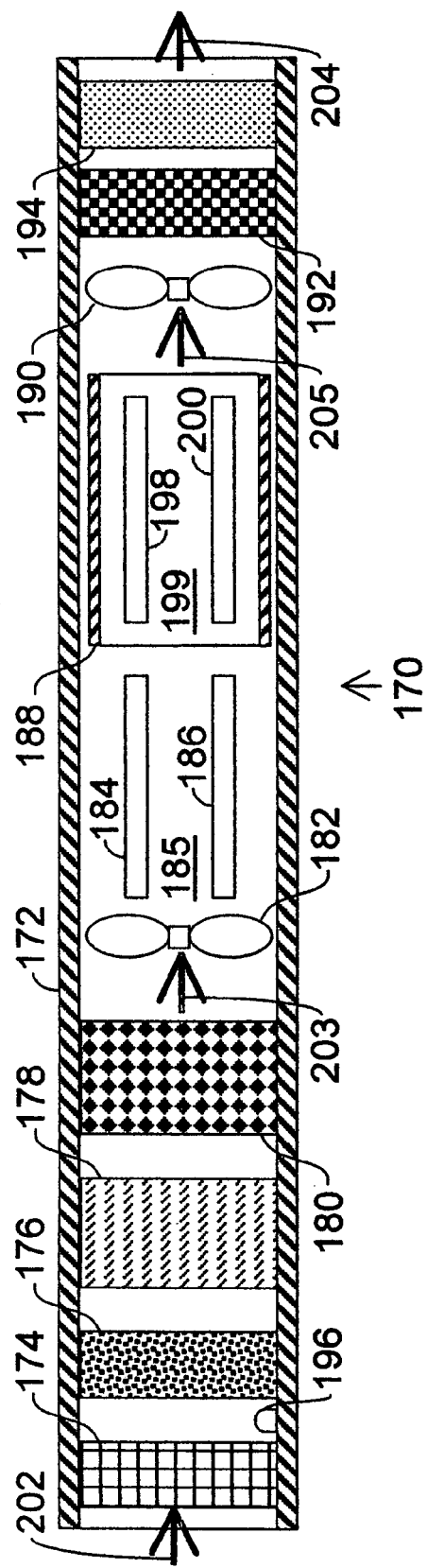
FIG. 11 is a diagrammatic illustration of another embodiment of the instant invention.
Figure 12:
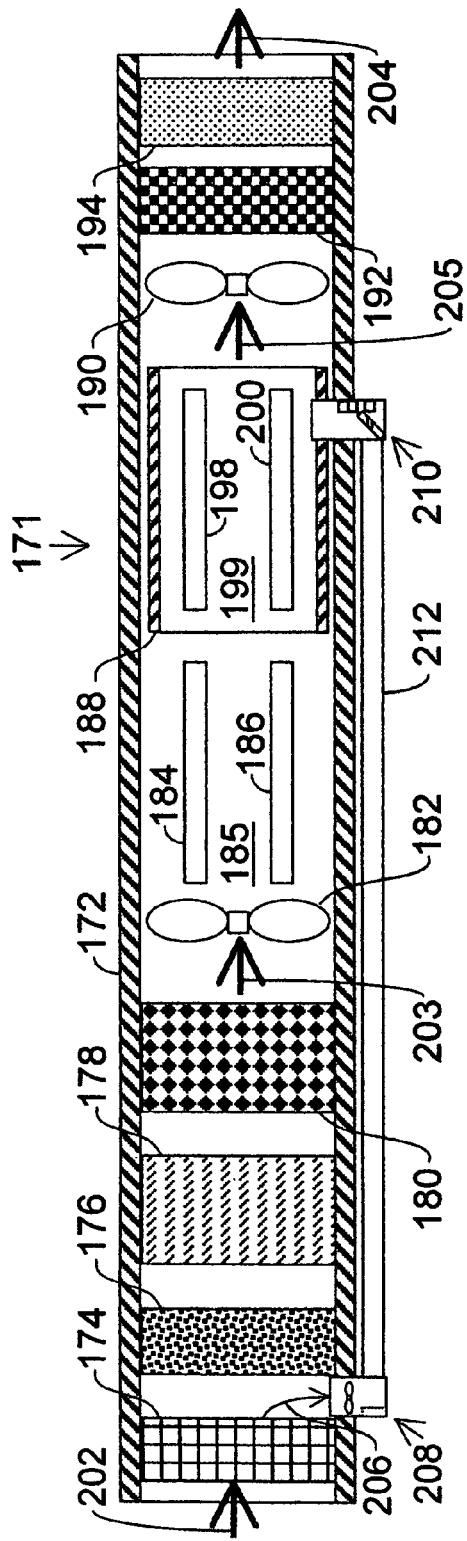
FIG. 12 is a diagrammatic illustration of yet another embodiment of the instant invention.
Figure 13:
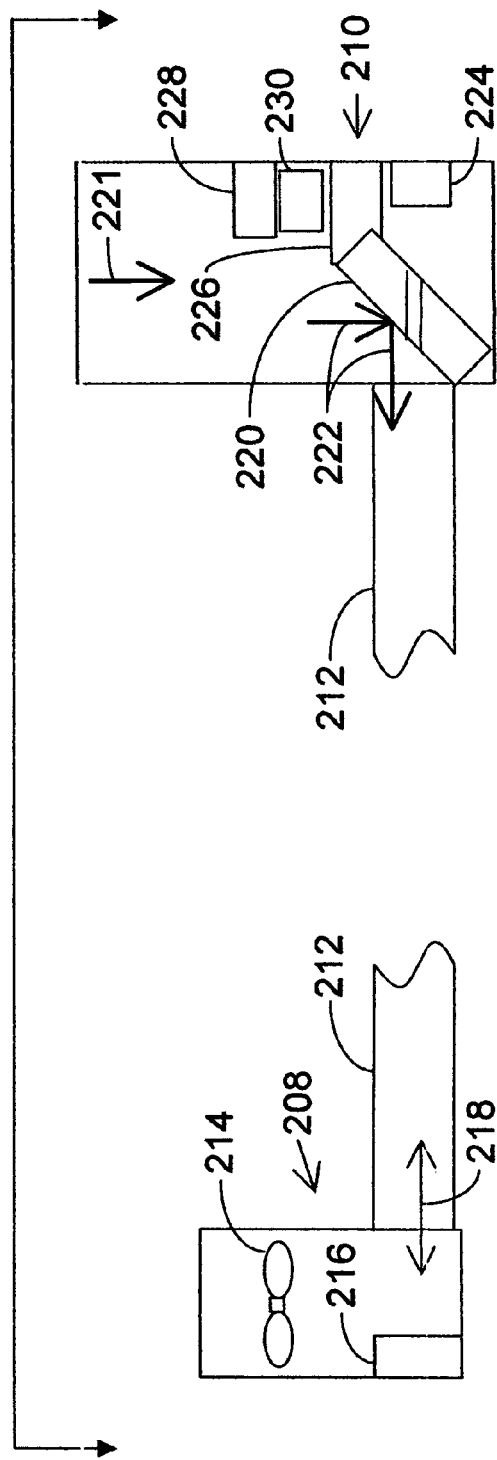
FIG. 13 is an expanded view showing particulars of construction of the embodiment of FIG. 12.

FIG. 11 illustrates another embodiment with additional features added to support generation and control of ozonites in addition to generation of ozone. In addition to a rough filter 174 used to remove coarse particulates and fibers, this embodiment may also include an activated charcoal filter 176, a humidification stage 178, or a separate stage for injection of other reagents 180. In addition, this embodiment provides for a post-injector 192 or a separate activated filter or catalyst stage 194. One or more fans 182, 190 may be placed at different positions within a generally tubular duct 172 used to contain and support components of this unit 170. Placement of fans among other components may be determined by a need to avoid potentially corrosive effects of some reagents on a fan or motor or by a need to generate turbulent flow within portions of an air stream, particularly around VUV lamps 184, 186 or UV-C lamps 198, 200. A reflector 188 may also be used around UV-C lamps 198, 200, VUV lamps 184, 186, or both sets of lamps, as needed or desired to enhance separate effects of each type of radiation, explained earlier herein. This embodiment also shows an ozone sensor 196 located just behind rough filter 184 in order to provide a capability to monitor ozone levels in entering air stream 202. Ozone sensor 196 may be of a metal oxide type, such as a MICS-2610 ozone sensor marketed by MicroChemical Systems SA, Corcelles, Switzerland (info@microsystems.com), or of a different type capable of providing near real-time monitoring of changing ozone concentrations. In this embodiment, pre-conditioning components (filters 174, 176, humidifiers 178, or reagent injectors 180) are used to either remove or add substances to air stream 202 flowing through unit 170 into irradiation chambers 185 and 199 containing VUV lamps 184, 186 or UV-C lamps 198, 200, respectively.

Pre-conditioning stages may be designed, for example, to remove certain substances that might create a hazardous chemical when exposed to other reagents or VUV or UV-C radiation, but will more generally be used to add reagents such as water vapor, hydrogen peroxide, or other substances to air stream 202 in order to enhance certain reactions or to generate particular types of ozonites upon exposure of a resulting air stream 203 to VUV or UV-C radiation. Post-conditioning stages 192, 194, may be designed to remove substances from air stream 205 that may be undesirable to exhaust into an area being treated. Post-conditioning stages 192, 194 may also be used, however, to add substances to exiting air stream 204. For example, additional humidification may be added to air stream 204 in order to promote humidification and blooming of fungal spores in an area being treated making them more susceptible to oxidation and neutralization by ozone contained in exhaust air 204. Humidification stage 178 may be any of several types, including, for example, evaporation belts, Seltzer pads, centrifugal injectors, ultrasonic atomization injectors, or one or more high pressure atomization jets or nozzles. Similar techniques may also be used to impart other reagents into air stream 205 in a separate reagent injection stage 180. Similar techniques may also be used in a post-conditioning injection stage 192, which may be placed before or after a post-conditioning filter stage 194, depending upon desired chemical reactions, in order to control chemical composition of exhaust air stream 204. A control system for this embodiment may be similar to controls already disclosed herein for earlier embodiments, but with a possible addition of separate controls for removal or impartation of humidity or other reagents to incoming air stream 202 or for control of removal or impartation of substances to exiting air stream 204. Although not shown, other sensors may be added to such an embodiment to monitor concentrations of reagents being injected or to monitor concentrations of substances in intake or exhaust air streams. Unit 170 could also be connected via wire, fiber, or wireless connection to other sensors located remotely from unit 170 to provide a capability for monitoring and controlling concentrations in a treated area at some distance from unit 170 itself. Embodiments employing sensors located remotely from a unit 170 may be used to further exploit a concept described earlier herein for creation of closed loop feedback treatment systems making use of one or more units such as unit 170, unit 4, unit 160, or similar units that may be developed based upon disclosures herein.

FIG. 12 illustrates another embodiment similar to that of FIG. 11, but having metal oxide ozone sensor 196 (FIG. 11) replaced with an alternative type of ozone sensor based upon attenuation by ozone of UV-C wavelength (254 nm) radiation produced by UV-C sources 198, 200. In the embodiment of FIG. 12 (and referring also to expanded views in FIG. 13 of components at either end of an enclosed passageway 212), a path is provided for sampling 206 of incoming air stream 202 preferably at a position behind rough filter 174 so as to avoid contamination with large particulates or fibers, but generally positioned ahead of other pre-conditioning components to avoid interference from other agents injected into air stream 202. Depending upon pressure differentials created by locations of one or more main airflow fans 182, 190, it may be desirable to provide a miniature fan 214, such as those used for cooling of micro-processors, near an intake of air stream sampling passageway 212 so as to ensure an air flow in a direction indicated 206 through the sampling passageway 212. An opposite end of air sample passageway 212 enters a fitting 210 positioned so as to be able to receive direct UV-C radiation from either of UV-C tubes 198, 200. A control photo-detector 230 is used to monitor intensity of a UV-C source 198, 200 through a minimal air gap. A filter, an aperture plate with a small hole, or similar device 228 may be used to reduce radiation arriving at control photo-detector 230 in a controlled manner so as to avoid saturation of photo-detector 230. In the embodiment shown, a mirror 220 is used within fitting 210 to reflect a portion of incoming light stream 221, 222 down the length of air sample passageway 212 so as to reflect from a retro-reflective device 216 located at an opposite end of passageway 212 through which air sample 206 is induced to flow. A portion of retro-reflected light 218 is allowed to reach another photo-detector 224 through a small hole in mirror 220. Second photo-detector 224 is protected from direct radiation from UV-C sources 198, 200 by light-tight components 226. After initial comparative calibration of photo-detectors 230 and 224 (e.g., for dark current and sensitivity), concentrations of ozone in intake air sample 206 may be determined by a comparison of the output of control photo-detector 230 with the output of second photo-detector 224 since UV-C radiation reaching second photo-detector 224 will be attenuated by an amount related to a concentration of ozone within sample passageway 212. In some embodiments similar to that just described, particularly where UV-C source 198, 200 is very intense, it may be desirable to add a filter or aperture plate within light path 221, 222 from UV-C source 198, 200, but before light 221, 222 enters sample passageway 212 in order to prevent overly intense UV-C light from appreciably interacting with and thereby reducing concentrations of ozone as ozone travels through sample passageway 212, which would interfere with an ability to measure an un-attenuated concentration of ozone in an ambient intake air flow 202. Such a filter or other attenuation device placed in light path 221, 222 just described would also help prevent saturation of second photo-detector 224. A narrow bandpass filter with a center wavelength near 254 nm may also be used between the hole in mirror 220 and photo-detector 224 to attenuate radiation at wavelengths to either side of a desired 254 nm to reduce influence of stray light reaching photo-detector 224. Many alternative embodiments are possible based upon a general principle of using a portion of UV-C radiation from a UV-C source being used to treat an air stream 203 to also monitor attenuation of UV-C radiation by an ozone concentration entering an air sampling passageway. By using other fittings and air sample passageways, ozone concentrations in exiting air stream 204, or at intermediate flow stages within unit 171, may also be monitored. In an alternative embodiment, a beam splitter might be used in place of mirror 220 and control photo-detector 230 might be positioned below a beam splitter but in a position where it is still able to directly view a UV-C source through a controlled attenuation device 228. In various embodiments, collimating tubes or baffles might be added to control flow of light to each of photo-detectors 230, 224 to ensure that only radiation that has traveled an intended path reaches each detector (e.g., in the case of second photo-detector 224, light that has traveled through sample passageway 212 and been retro-reflected from retro-reflector 216). Retro-reflector 216 may be an inexpensive retro-reflector such as those found in bicycle reflectors, and preferably one that provides minor divergence of a reflected beam so as to ensure some retro-reflected light travels through a hole in mirror 220 to second photo-detector 224. Sample passageway 212 might be a separate standalone tube as illustrated in FIG. 12 or it may be a passageway molded into a structure of duct 172 or a tube fixed to an interior of duct 172. As noted, separate passageways and fittings similar to those illustrated might also be used to monitor concentrations of ozone in exiting air stream 204 or at other stages within unit 171.

As explained for the embodiment illustrated in FIG. 11, a set of controls similar to those disclosed for earlier embodiments might also be implemented for control of different stages, components, and modes of operation of unit 171 in order to provide control of generation and release of ozone, ozonites, and other compounds to provide desired types and levels of treatment of incoming air or air within an area being treated.

Having thus disclosed my invention and the manner of its use, it should be apparent that incidental changes may be made thereto that fairly fall within the scope of the following appended claims, wherein I claim:

The invention claimed is:

1. A method for purifying air of a space, said method comprising:
    circulating, repeatedly, said air from said space through a housing and back to said space, said air entering at least one entrance of said housing and exiting at least one exit of said housing;
    oxidizing said air while within said housing at least one first ultraviolet radiation generator that radiates said air for at least one first time interval, and emitting air containing ozone from said housing to said space for said at least one first time interval to at least sterilize, sanitize or purify said space; and,
    returning said air containing ozone from said space to said housing and eliminating said ozone from said air in said housing at least one second ultraviolet radiation generator and emitting air free of ozone to said space from said housing during at least one second time interval.

2. The method of claim 1 further comprising producing a first ultraviolet radiation that generates said ozone using said at least one first ultraviolet radiation generator.

3. The method of claim 1, further comprising the step of:
    preventing said first ultraviolet radiation from escaping said housing.

4. The method of claim 1 further comprising producing a second ultraviolet radiation that destroys said ozone using, said at least one second ultraviolet radiation generator.

5. The method of claim 1, further comprising the step of:
    preventing said second ultraviolet radiation from escaping said housing.

6. The method of claim 1, further comprising the step of:
    filtering at least some particles that would otherwise enter said housing.

7. The method of claim 1, further comprising the step of:
    filtering, using a reactive filter, residual amounts of said ozone from said air.

* * * * *